US005939467A

United States Patent [19]

Wnuk et al.

[11] Patent Number: 5,939,467
[45] Date of Patent: *Aug. 17, 1999

[54] BIODEGRADABLE POLYMERIC COMPOSITIONS AND PRODUCTS THEREOF

[75] Inventors: Andrew Julian Wnuk, Wyoming; David Harry Melik, Fairfield; Terrill Alan Young, Cincinnati, all of Ohio

[73] Assignee: The Procter & Gamble Company, Cincinnati, Ohio

[ * ] Notice: This patent issued on a continued prosecution application filed under 37 CFR 1.53(d), and is subject to the twenty year patent term provisions of 35 U.S.C. 154(a)(2).

[21] Appl. No.: 08/308,066

[22] Filed: Sep. 16, 1994

Related U.S. Application Data

[63] Continuation-in-part of application No. 07/904,776, Jun. 26, 1992, abandoned.

[51] Int. Cl.⁶ .............................. C08L 67/04; C08L 75/06
[52] U.S. Cl. .......................... 523/128; 523/124; 524/503; 524/507; 524/517; 524/522; 524/58; 524/411; 524/413; 524/450; 524/903
[58] Field of Search .............................. 525/58, 411, 413, 525/415, 450, 903; 524/43, 41, 40, 39, 38, 37, 47, 503, 539, 507, 517, 522; 523/124, 125, 128

[56] References Cited

U.S. PATENT DOCUMENTS

| | | | |
|---|---|---|---|
| 3,668,157 | 6/1972 | Combs et al. | 260/13 |
| 3,809,088 | 5/1974 | Ulrich, Jr. | 128/285 |
| 3,867,324 | 2/1975 | Clendinning et al. | 260/23 H |
| 3,922,239 | 11/1975 | Koleske et al. | 260/13 |
| 3,931,068 | 1/1976 | Clendinning et al. | 260/7.5 |
| 3,949,145 | 4/1976 | Otey et al. | 428/423 |
| 4,002,171 | 1/1977 | Taft | 128/284 |
| 4,011,871 | 3/1977 | Taft | 128/284 |
| 4,132,839 | 1/1979 | Marans et al. | 521/159 |
| 4,133,784 | 1/1979 | Otey et al. | 260/17.4 ST |
| 4,284,671 | 8/1981 | Cancio et al. | 428/35 |
| 4,337,181 | 6/1982 | Otey et al. | 523/128 |
| 4,372,311 | 2/1983 | Potts | 128/287 |
| 4,454,268 | 6/1984 | Otey et al. | 524/47 |
| 4,673,438 | 6/1987 | Wittwer et al. | 106/126 |
| 4,745,160 | 5/1988 | Churchill | 525/415 |
| 4,873,270 | 10/1989 | Aime et al. | 523/128 |
| 4,880,592 | 11/1989 | Martini et al. | 264/514 |
| 4,915,893 | 4/1990 | Gogolewski et al. | 264/205 |
| 4,916,193 | 4/1990 | Tang et al. | 525/413 |
| 4,964,857 | 10/1990 | Osborn | 604/395 |
| 5,095,054 | 3/1992 | Lay et al. | 524/47 |
| 5,097,005 | 3/1992 | Tietz | 528/272 |
| 5,124,371 | 6/1992 | Tokiwa et al. | 525/450 |
| 5,166,232 | 11/1992 | Muller et al. | 524/35 |
| 5,169,889 | 12/1992 | Kauffman et al. | 524/272 |
| 5,171,308 | 12/1992 | Gallagher et al. | 604/372 |
| 5,171,309 | 12/1992 | Gallagher et al. | 604/365 |
| 5,185,009 | 2/1993 | Sitnam | 604/364 |
| 5,190,533 | 3/1993 | Blackburn | 604/367 |
| 5,196,247 | 3/1993 | Wu et al. | 428/43 |
| 5,217,803 | 6/1993 | McBride et al. | 428/323 |
| 5,227,415 | 7/1993 | Masuda et al. | 524/17 |
| 5,231,148 | 7/1993 | Kleinke et al. | 525/450 |
| 5,252,648 | 10/1993 | Iovine et al. | 524/270 |
| 5,254,607 | 10/1993 | McBride et al. | 524/47 |
| 5,286,770 | 2/1994 | Bastioli et al. | 524/47 |
| 5,466,517 | 11/1995 | Eschweg et al. | 428/288 |

FOREIGN PATENT DOCUMENTS

| | | |
|---|---|---|
| 0 226 439 A1 | 6/1987 | European Pat. Off. . |
| 0 326 517 A1 | 8/1989 | European Pat. Off. . |
| 0 327 505 A2 | 8/1989 | European Pat. Off. . |
| 0 344 118 A2 | 11/1989 | European Pat. Off. . |
| 0 400 531 A1 | 12/1990 | European Pat. Off. . |
| 0 400 532 A1 | 12/1990 | European Pat. Off. . |
| 0 408 503 A2 | 1/1991 | European Pat. Off. . |
| 0 409 781 A2 | 1/1991 | European Pat. Off. . |
| 0 409 782 A2 | 1/1991 | European Pat. Off. . |
| 0 435 435 A2 | 7/1991 | European Pat. Off. . |
| 0 449 041 A2 | 10/1991 | European Pat. Off. . |
| 0 450 777 A2 | 10/1991 | European Pat. Off. . |
| 0 512 360 A1 | 11/1992 | European Pat. Off. . |
| 0 525 245 A1 | 2/1993 | European Pat. Off. . |
| 0 533 144 A2 | 3/1993 | European Pat. Off. . |
| 0 566 357 A1 | 10/1993 | European Pat. Off. ........ C08L 67/04 |
| 0 606 923 A2 | 7/1994 | European Pat. Off. ........ C08L 67/04 |
| 0 629 662 A1 | 12/1994 | European Pat. Off. ........ C08L 67/04 |
| 4016348A1 | 11/1991 | Germany . |
| 4119455C1 | 9/1992 | Germany . |
| 2-222421 | 9/1990 | Japan . |
| 4-93315 | 3/1992 | Japan . |
| 4-178 466 | 6/1992 | Japan . |
| 2243327 | 10/1991 | United Kingdom . |
| WO 90/10671 | 9/1990 | WIPO . |

(List continued on next page.)

OTHER PUBLICATIONS

Poly (3–hydroxybutyrate)–co–(3–hydroxyvalerate)/Poly–L– Lactide Blends: Thermal and Mechanical Properties, *Journal of Applied Polymer Science*, vol. 54 (1994), pp. 1525–1535.

(List continued on next page.)

*Primary Examiner*—Peter A. Szekely
*Attorney, Agent, or Firm*—Bart S. Hersko; Edward J. Milbrada; Loretta J. Henderson

[57] ABSTRACT

The present invention relates to polymeric compositions that are biodegradable and that can be melt processed into various forms, including films, fibers, and nonwovens. The compositions include compatible or semicompatible blends of biodegradable polymers and have physical and thermomechanical integrity. Films formed from preferred polymeric compositions are suitable for use as backsheets in disposable absorbent articles. In a preferred embodiment, the polymeric composition includes a polyhydroxyalkanoate and at least one other biodegradable polymer selected from aliphatic polyester-based polyurethanes, a polylactide, polycaprolactone, or a mixture of two or more of these polymers. Where the second polymer is polycaprolactone, the composition preferably also includes a third polymer for enhancing the melt processability of the composition.

8 Claims, No Drawings

FOREIGN PATENT DOCUMENTS

| | | | |
|---|---|---|---|
| WO 91/02023 | 2/1991 | WIPO . | |
| WO 91/02024 | 2/1991 | WIPO . | |
| WO 91/08726 | 6/1991 | WIPO . | |
| WO 91/13207 | 9/1991 | WIPO . | |
| WO 92/01733 | 2/1992 | WIPO . | |
| WO 92/04410 | 3/1992 | WIPO . | |
| WO 92/09654 | 6/1992 | WIPO . | |
| WO 92/15454 | 9/1992 | WIPO . | |
| WO 92/19680 | 11/1992 | WIPO . | |
| WO 93/00116 | 1/1993 | WIPO . | |
| WO 93/00399 | 1/1993 | WIPO . | |
| WO 93/03098 | 2/1993 | WIPO . | |
| WO 94/00506 | 1/1994 | WIPO . | |
| WO 94/06866 | 3/1994 | WIPO . | |
| WO 94/11440 | 5/1994 | WIPO | C08L 67/04 |
| WO 94/11445 | 5/1994 | WIPO | C08L 101/100 |
| WO 91/02025 | 2/1995 | WIPO . | |

OTHER PUBLICATIONS

Properties of Poly-β-Hydroxyalkanoate Latex: Nascent Morphology, Film Formation and Surface Chemistry; Marchessault et al.

Influence of Copolymer Structure on Properties of Poly-β-Hydroxyalkanoates; Marchessault et al.; Polym. Mater. Sci. Eng. 62 pp. 226–230 (1990).

Microbial Synthesis and Characterization of Poly (3–hydroxybutyrate–co–3–hydroxypropionate); E. Shimamura, et al., Macromolecules 27, pp. 4429–4435 (1994).

Morphological and Blend Miscibility Effects on the Biodegradability of Poly (3–Hydroxybutyrate–co–3–Hydroxyvalerate) and Blends; P. Dave et al., Polym. Mater. Sci. Eng. 63, pp. 726–731 (1990).

Miscibility and Morphology of Blends if Isotactic and Atactic Poly (3–hydroxybutyrate); H. Abe, et al.; Macromolecules 27, pp. 50–54 (1994).

Physical Properties of Poly(β–hydroxybutyrate) –Poly (ε–caprolactone) Blends; F. Gassner et al.; Polymer Report 35, pp. 2233–2236 (Nov. 10, 1994).

Derwent Publications Ltd., abstract No. 90–315322 (JO 2222–421–A–Japan); Biodegradable composite material for packing film; Chuko Kasei Kogyo K (Sep. 5, 1990).

Derwent Publications Ltd., abstract No. 92–155471 (JPA 4093315–Japan); Preparation of biodegradable, high strength resin composition for containers,etc.; Denki Kagaku Kogyo (Mar. 26, 1992).

Derwent Publications Ltd., abstract No. 92–263106 (JPA 4178466–Japan); Naturally degradable polymer composition, used for packing films; Shingijutsu Kaihatsu Jigyodan (Jun. 25, 1992).

Derwent Publications Ltd., abstract No. 92–09300/12 (JO 4036–320–A) Mfg. biodegradable copolymer for sheets, films, coatings, etc. –by heating and melting mixt. of lactone cpd. and polyamide; Kao Corp. (Feb. 6, 1992).

Derwent Publications Ltd., abstract No. 93–120862/15 (JP 05057833–A) Microorganism degradable multiply sheet useful for packaging –comprises intermediate sheet layer produced from starch and/or plant protein and resin sheet layers laminated to opposite sides of intermediate layer; JSP Corp. (Mar. 9, 1993).

Derwent Publications Ltd., abstract No. 91–289517/40 (EP 449041–A); Cellulose hydrate–polyurethane(urea) blends – giving biodegradable, crackle–free films useful in packaging mulch or silo films, transparent paper etc.; Wolff Walsrode AG (Oct. 2, 1991).

U.S. Application No. 08/128,041, Toms and Wnuk; "Disposable Absorbent Articles with Biodegradable Backsheets;" filed Sep. 27, 1993.

U.S. Application No. 08/138,570, Toms and Wnuk; "Biodegradable, Liquid Impervious Films;" filed Oct. 18, 1993.

U.S. Application No. 08/126,672; Wnuk and Koger; "Biodegradable, Liquid Impervious Multilayer Film Compositions;" filed Sep. 24, 1993; allowed on Sep. 2, 1994.

U.S. Application No. 08/189,015; filed Jan. 28, 1994.

U.S. Application No. 08,189,029; filed Jan. 28, 1994.

U.S. Application No. 08/188,271; filed Jan. 28, 1994.

U.S. Application No. 08/247,539; filed May 23, 1994.

U.S. Application No. 07/721,794; McBride et al. "Biodegradable, Liquid Empervious Films;" filed Jun. 26, 1991.

BIODEGRADABLE POLYMERIC COMPOSITIONS AND PRODUCTS THEREOF

This is a continuation-in-part of application Ser. No. 07/904,776, filed on Jun. 26, 1992, now abandoned.

TECHNICAL FIELD

The present invention relates to polymeric compositions that are biodegradable and that can be melt processed into various forms, including films, fibers, and nonwovens, which products have substantially uniform physical properties, and physical and thermomechanical integrity. Films formed from preferred polymeric compositions are suitable for use as backsheets in articles such as diapers, sanitary napkins, pantiliners, and the like, which are adapted for absorbing various bodily fluids.

BACKGROUND OF THE INVENTION

Several polymers have been described in the art as being degradable, biodegradable, compostable, and the like. However, the polymers typically suffer from some limitation in physical properties which detracts from their utility in a number of applications. For example, for economic reasons it is typically desirable to process polymers by a melt process such as melt spinning, cast film extrusion, or blown film extrusion. However, the melt strength and/or set time of the polymer may not be suitable for good melt processing. Thus, the product tends to tear, break, or stick during processing, or the product may be unacceptably nonuniform in its physical properties. Once processed, still other properties may be needed to meet the converting, storage (including shipping and warehouse storage), or end use requirements of the polymeric product. More particularly, the product may need certain mechanical and thermomechanical properties to withstand subsequent processing and storage, and to meet end use requirements.

In addition, although several polymeric materials have been described as biodegradable, not all biodegradable materials are readily compostable. In general, for a material to be compostable, the polymeric product or large fragments thereof must undergo an initial breakup to much smaller fragments during the initial stages of a typical, commercial composting process. Otherwise, the products or large fragments may be screened out of the compost stream and may never become part of the final compost.

In commercial composting processes, the product is typically exposed to mechanical action, elevated temperatures, and/or moisture to promote the initial breakup of the product or large fragments thereof to much smaller fragments. Many biodegradable polymers exist which are sensitive to mechanical action, elevated temperatures, or moisture, such that they would individually meet the initial requirements for composting. However, few, if any, also possess the mechanical, thermomechanical, and other properties required for their practical use in a number of applications.

One practical application of biodegradable polymeric materials is in disposable absorbent articles. Although disposable absorbent articles largely comprise materials which would be expected ultimately to degrade, and although articles of this type contribute only a very small percentage of the total solid waste materials generated by consumers each year, nevertheless, there is currently a perceived need to devise such disposable products from materials which are more readily biodegraded and, preferably, which are more readily composted. There is a particular perceived need to replace polyethylene backsheets in absorbent articles with liquid impervious films of biodegradable material, since the backsheet is typically one of the largest non-biodegradable components of a conventional disposable absorbent article.

In addition to being biodegradable, the films employed as backsheets for absorbent articles must satisfy many other performance requirements. For example, the polymer must be thermoplastic if economical, conventional, film melt processing methods, such as cast film and blown film extrusion and extrusion coating, are to be employed. Preferred materials can be melt processed into films that have substantially uniform physical properties and physical integrity. In addition, the film should have sufficient thermomechanical integrity. Thus, upon exposure to elevated temperatures, the film should maintain sufficient physical integrity to enable it to function as required at the elevated temperature, for example, to enable it to survive converting processes. In addition, even after exposure to elevated temperatures, the film should have substantial physical integrity. The film should also have certain properties to meet end use requirements. More particularly, properties such as tensile strength, tensile modulus, tear strength, impact strength, and moisture transmission rate are important since they influence the absorbent article's durability and containment while being worn.

It is an object of the present invention to provide a polymeric composition that is biodegradable and which can be melt processed to form products having substantially uniform physical properties and physical integrity. Another object is to provide such a polymeric composition that also has thermomechanical integrity. Thus, upon exposure to elevated temperatures, a product thereof should maintain sufficient physical integrity to enable it to function as required at the elevated temperature, for example, to enable it to survive converting processes. In addition, even after exposure to elevated temperatures, the product should have mechanical and other properties which enable it to be suitable for use in a number of practical applications. It is a further object of the invention to provide such a polymeric composition that can be used to form more readily compostable products. Another object of the present invention is to provide such products in the form of a fiber, nonwoven, or film. Yet another object of the present invention is to provide disposable absorbent articles such as disposable diapers, catamenials, and the like, having component parts formed from such products.

It is a particular object of the present invention to provide biodegradable, liquid impervious films suitable for use in absorbent articles, wherein the film has each of the following properties at room temperature:

a) a machine direction (MD) tensile modulus of from about 10,000 to about 100,000 lbs/in$^2$ (6.895×10$^8$ dynes/cm$^2$ to 6.895×10$^9$ dynes/cm$^2$; 68.95 MPa to 689.5 MPa);

b) a machine direction tear strength of at least about 25 grams per 25.4 microns (25.4 micrometers, 1 mil) of thickness;

c) a cross machine direction (CD) tear strength of at least about 25 grams per 25.4 microns (25.4 micrometers, 1 mil) of thickness;

d) an impact strength of at least 12 cm as measured by falling ball drop;

e) a moisture transport rate of less than about 0.0012 grams per square centimeter per 16 hours; and f) a thickness of from about 12 microns (12 micrometers, 0.5 mils) to about 75 microns (75 micrometers, 3 mils).

Preferred films also have, at room temperature and in the machine direction of manufacture, an elongation at break of at least about 140% and a tensile strength of at least 20 MPa. In addition, preferred films have a failure temperature, as defined herein, of at least about 60° C.

SUMMARY OF THE INVENTION

The present invention is directed to polymeric compositions that are biodegradable and that can be melt processed into various forms, including films, fibers, and nonwovens. The compositions have melt strengths and set times that enable products to be directly formed by conventional melt processing techniques. In addition, the compositions provide products having physical integrity and substantially uniform physical properties, including mechanical properties, which enable their use in a number of practical applications. Preferred compositions are useful for forming films or fibers which are suitable, respectively, for use as backsheets or in topsheets in disposable absorbent articles. Products of preferred polymeric compositions also have thermomechanical integrity as described herein.

The polymeric compositions contain two or more biodegradable polymers, at least two of the polymers having different primary limitations on their utility in forming biodegradable, melt processable products having physical integrity, suitable physical properties, and/or thermomechanical integrity. The primary limitations may be moisture sensitivity, thermal sensitivity, mechanical limitations, difficulty in melt processing (generally influenced by melt strength and/or set time), or capability of size reduction, for example, in commercial composters. The compositions of the present invention overcome the primary limitations of the individual components and at the same time provide certain performance properties to the end product. The compositions include compatible or semicompatible blends of polymers.

In a preferred embodiment, the polymeric composition includes a first, biodegradable polymer, which is a polyhydroxyalkanoate; and at least one second, biodegradable polymer that is selected from aliphatic polyester-based polyurethanes, polylactides, polycaprolactone, or a mixture of two or more of these polymers. Where the second polymer is a polylactide, the composition preferably also includes a plasticizer. Where the second polymer is polycaprolactone, the composition preferably also includes an additional polymer for enhancing the melt processability of the composition. The additional polymer may alternatively be a polylactide, an aliphatic, polyester-based polyurethane, a thermoplastic poly(vinyl alcohol) composition, a starch-based interpenetrating network, hydroxypropylcellulose, a cellulose ester, or a mixture thereof.

The compositions of the present invention are useful for forming biodegradable, liquid impervious films. Preferred blends can be melt extruded to form biodegradable films having mechanical and thermomechanical properties that are preferred, for example, for use in backsheet applications. The compositions are also useful for forming fibers, for example, by melt spinning processes, and nonwoven materials containing such fibers. The nonwovens are useful, for example, as a biodegradable topsheet in disposable absorbent articles.

The present invention also encompasses disposable absorbent articles having a liquid pervious topsheet, a liquid impervious backsheet, and an absorbent core positioned between the topsheet and the backsheet, the articles being characterized by including the biodegradable polymeric composition. In preferred embodiments, the topsheet includes a nonwoven web of fibers formed from the polymeric composition and/or the backsheet includes a film formed from the polymeric composition.

DETAILED DESCRIPTION OF THE INVENTION

The present invention is directed to polymeric compositions that are biodegradable and that can be melt processed into various forms, including films, fibers, and nonwovens. The compositions have melt strengths and set times that enable products to be directly formed by conventional melt processing techniques. In addition, the compositions provide products having physical integrity and substantially uniform physical properties, including mechanical properties.

As used herein, the product has physical integrity if it is substantially free from physical defects or flaws which significantly reduce the utility of the product for its intended application, and further is substantially whole in its intended form (i.e., integral). Flaws or defects include, for example, holes, tears, breaks, cracks, folds, nonuniformities in thickness, distortions in shape, and the like, which significantly reduce the utility of the product for its intended application.

The compositions provide products having physical properties, including mechanical properties, which enable their use in a number of practical applications. Preferred compositions are useful for forming films or fibers which have physical properties that are preferred as described herein, respectively, for use as backsheets or in topsheets of disposable absorbent articles. The physical properties of the products formed from the compositions of the present invention are substantially uniform. The polymeric products herein thus have substantial uniformity of properties in the machine direction of manufacture and, in the case of films, in the cross machine direction of manufacture. It will be recognized by the skilled artisan that, for products formed by a melt process, the physical properties in the machine direction typically differ from the physical properties in the cross machine direction.

Products of preferred polymeric compositions also have thermomechanical integrity up to a given temperature that is above room temperature. As used herein, room temperature refers to temperatures in the range of 20° C. to 25° C. As used herein, a product of a polymer or composition has thermomechanical integrity up to such a given temperature if it maintains sufficient physical integrity upon exposure to that temperature, such that it is suitable for use in its intended application after exposure to that temperature. It is to be understood that the intended application may be at room temperature, or above or below room temperature. In general, the product must remain strong enough upon and after exposure to the temperature that is above room temperature such that it is suitable for use in its intended application after exposure to that temperature. After exposure to the temperature that is above room temperature, the product has physical properties, including mechanical properties, such that it is suitable for its intended use.

As will be understood by the skilled artisan, thermomechanical integrity is a function of the conditions of exposure, including time and temperature, that would be expected to be realized for a given application. Thus, strength retention tends to depend on the length of time of exposure to the temperature that is above room temperature. In general, for a given exposure time, the strength decreases to a greater extent and/or more rapidly as the exposure temperature increases. On the other hand, under nonequilibrium conditions the strength decreases to a greater extent as the exposure time increases, for a given exposure temperature. Under equilibrium conditions, the strength does not change with time at a given temperature.

For example, a backsheet film or other article component may be exposed to temperatures that are above room temperature during storage or fabrication of the absorbent article. Disposable absorbent articles may be exposed, for example, to temperatures as high as 60° C. during storage of the article. Moreover, during fabrication of disposable absorbent articles (i.e., during converting processes or conversion of disposable absorbent articles), a portion or all of a backsheet film or other component of the article may be exposed to temperatures in excess of about 65° C. In particular, the conversion process may involve exposure to temperatures ranging from about 65° C. to about 90° C. The component may be exposed to even higher temperatures, for example, during hot-melt gluing operations. Hot-melt gluing operations may expose the article component, either directly or environmentally, to temperatures ranging from about 120° C. to about 240° C. The skilled artisan will understand that the amount of time and proximity of exposure to such temperatures may vary such that the effective temperature realized by the component may actually be less than the noted temperatures.

The backsheet or other article component has thermomechanical integrity up to a given temperature that is above room temperature and that may be encountered during storage or fabrication, if at that given temperature it maintains sufficient physical integrity upon exposure to that temperature for a time period which would be considered typical by the skilled artisan, such that it is suitable for use in its intended function in the article after such exposure. The article component must remain strong enough upon and after exposure to the given temperature that is above room temperature such that it is suitable for use in its intended function in the article after that exposure. After exposure to the given temperature that is above room temperature, the article has physical properties, including mechanical properties, such that it is suitable for its intended function in the article.

The thermomechanical integrity of a polymeric product can be described by the failure temperature of the product. In general, the failure temperature as used herein is the temperature at which the dynamic storage modulus in tension (E') of a polymer product falls below a minimum value required for the product to function in its intended application, (including secondary processes such as conversion processes, and end use applications). The dynamic storage modulus in tension of a polymeric product as a function of temperature can be determined using a dynamic mechanical analysis technique as described herein (the dynamic storage modulus in tension is alternatively referred to herein as DSM). The failure temperature can then be determined by noting the temperature at which the DSM falls below the value that is required for the product to function in its intended application.

Typically, the DSM of a polymeric product decreases monotonically with increasing temperature, and the polymer product will exhibit a significant, maximum decrease in the DSM which is initiated at or near the failure temperature. (A significant decrease in the DSM may also be initiated at other temperatures below the failure temperature, for example, at the glass transition temperature of the polymer product. However, the decrease in DSM that begins at or near the failure temperature is greater than at these other temperatures. Typically, the change in DSM that occurs beginning at or near the failure temperature is on the order of at least two orders of magnitude over a positive temperature change of about 10° C.)

The failure temperature of polymeric films or fibers that are to be used in disposable absorbent articles, for example, as backsheets or in topsheets, respectively, is the temperature at which the DSM of the film or fiber falls below 20 MPa. Preferred compositions of the present invention provide polymeric films or fibers having a failure temperature of at least about 60° C., more preferably at least about 90° C., even more preferably at least about 110° C., most preferably at least about 120° C.

Stated another way, films or fibers that are to be used as backsheets or in topsheets in disposable absorbent articles preferably have a DSM of at least 20 MPa over the temperature range to which the film or fiber may be exposed during conversion, storage, or use. Preferred compositions of the present invention are those that provide films and fibers having a DSM of at least 20 MPa at a temperature of at least about 60° C., more preferably at least about 90° C., even more preferably at least about 110° C., most preferably at least about 120° C.

The compositions used to prepare the biodegradable products herein are derived from specific combinations of two or more biodegradable polymers. As used herein in reference to polymer components and compositions, "biodegradable," "biodegradability", "biodegradation" and the like means the capability of undergoing natural processes in which a material is broken down by metabolic processes of living organisms, principally fungi and bacteria. In the presence of oxygen (aerobic biodegradation), these metabolic processes yield carbon dioxide, water, biomass, and minerals. Under anaerobic conditions (anaerobic biodegradation), methane may additionally be produced.

The compositions of the present invention are also more readily composted than conventional materials such as polyethylene, as described in further detail herein in reference to disposable absorbent articles.

In general, the individual biodegradable polymers do not themselves meet all of the performance standards required for practical application in certain products, including disposable absorbent articles. More particularly, the individual polymers may not possess a melt strength and/or set time which is suitable for good melt processing, which is an economically preferred method of forming the types of polymeric products described herein. In addition, the products of the individual polymers may not have sufficient physical properties, including mechanical properties, to withstand subsequent processing, or for use in certain applications, for example, in disposable absorbent articles. In addition, a given polymer may not possess physical properties, such as tensile properties, tear strengths, an impact strength, and/or a moisture transmission rate, which are preferred for end use in absorbent articles. Moreover, the products of the individual polymers may not have thermomechanical integrity, such that the product exhibits an unacceptable loss in physical integrity or physical properties upon exposure to elevated temperatures, for example, during conversion or storage.

The individual polymers selected for the products of the invention are biodegradable polymers obtained from many sources, both natural and synthetic. Each of the polymers has one or more attributes which render it biodegradable. However, many of these attributes prevent the polymer from being used singularly as a material in certain biodegradable, preferably more readily composted, products. More specifically, many of these attributes prevent the polymer from being used singularly as a material in disposable absorbent articles, for example, as a monolayer backsheet in such articles.

For example, some biodegradable polymers are moisture sensitive. As used herein, "moisture sensitive polymer" means that the polymer, when exposed to aqueous media, may absorb significant amounts of water (e.g., more than about 10% by weight), swell, lose strength or stiffness, or may dissolve. The moisture sensitivity of materials to be used in absorbent articles is important, for example, insofar as it relates to the ability of the material to maintain its integrity during use of the article or to serve as a moisture barrier layer. For example, a film for use as a moisture barrier layer, e.g., a backsheet, preferably has a moisture transport rate of less than about 0.0012 grams per square centimeter per 16 hours. Examples of moisture sensitive polymers include interpenetrated networks of destructurized starch, polyvinylalcohol and related derivatives such as thermoplastic polyvinylalcohol compositions, and hydroxypropylcellulose and its derivatives.

Other biodegradable polymers suffer from their thermal sensitivity at relatively low process and/or storage temperatures. As used herein, "thermally sensitive polymer" means a polymer having a melting point of below about 65° C., an amorphous polymer having a glass transition temperature of less than about 65° C., or a polymer having a Vicat softening point of less than about 45° C. Such polymers are thermally sensitive due to these relatively low melting points or glass transition temperatures. Such polymers tend to exhibit thermoplastic flow at temperatures above their melting point or glass transition temperature and as a result are thermomechanically limited (The terms "thermally sensitive" and "thermomechanically limited" are used interchangeably herein). In addition, products formed from these polymers may lose their shape during storage at elevated temperatures. Examples of thermally sensitive polymers include aliphatic polyesters such as polycaprolactone, polyethylene adipate, polybutylene glutarate, and polypropylene succinate. Some aliphatic polyester-based polyurethanes are thermally sensitive as defined herein. In addition, polylactides may be thermally sensitive, depending on their structures. For example, non-crystalline polylactide, e.g., atactic polylactide or unannealed isotactic polylactide, tends to be thermally sensitive. The terms "atactic" and "isotactic" are defined in *Polymer Science Dictionary*, Mark S. M. Alger (Elsevier Applied Science 1990), incorporated herein by reference.

Still other polymers have mechanical deficiencies. By "mechanically limited polymer" it is meant that a product formed from the polymer is too stiff (tensile modulus too high), too soft (tensile modulus too low), suffers from poor tensile and/or tear strengths, and/or has insufficient elongation properties to enable its use in a given application. On the other hand, polymers or compositions that are not mechanically limited provide products that do not suffer from these limitations. For example, it is preferred that films for use in disposable absorbent articles and having a thickness of from about 12 microns to about 75 microns have, at room temperature, a machine direction (MD) tensile modulus from about 10,000 to about 100,000 lbs/in$^2$; a MD tear strength of at least 25 grams per 25.4 microns of thickness; a cross direction (CD) tear strength of at least 25 grams per 25.4 microns of thickness; and an impact strength of at least 12 cm as measured by falling ball drop; and more preferably also have, at room temperature, a tensile elongation at break of at least about 140% and a tensile strength of at least about 20 MPa. In the context of films, the mechanically limited polymers form films of the above-noted thickness having at least one of these properties outside of the stated ranges. Examples of mechanically limited polymers include cellulosic materials such as cellophane, cellulose esters, some blends of cellulose esters with aliphatic polyesters; polylactides, certain polyhydroxyalkanoates (e.g., PHBV copolymers), and some thermoplastic polyurethanes.

Other polymers are difficult to process by conventional melt processes, e.g., by cast film extrusion, blown film extrusion, and melt spinning processes, into films, fibers or other forms having physical integrity. By "polymer difficult to melt process," it is meant that the polymer exhibits an effective melt strength and/or set time that detracts from the ability to form products having physical integrity by a conventional melt extrusion process.

The effective melt strength refers to the resistance of a molten polymer to be drawn-down to a desired dimension such as thickness (in the case of films), or diameter or denier (in the case of fibers). A polymer having a low effective melt strength is unable to withstand the minimum strain that is required to draw the polymer melt to a desired dimension. For example, the polymeric material may exhibit instabilities such as breakage, sagging, or draw resonance. The resultant products tend to be highly nonuniform in physical integrity, e.g., the products have significant nonuniformities in thickness or shape.

The set time refers to the time period required, under a given set of process conditions, for the molten polymer material to achieve a substantially non-tacky physical state. The set time is important since, if the polymer does not set within a suitable time during processing, blocking may occur. Thus, the polymeric material having residual tack may stick to itself and/or to processing equipment even after cooling to room temperature or below. Such residual tack may restrict the speed at which the product can be processed or prevent the product from being collected in a form of suitable quality. Although blocking may be minimized by the use of conventional anti-block agents, it may sometimes be desirable to avoid the use of such agents, such that the polymer set time becomes especially important. For example, mineral anti-block agents such as talc, silica and the like may be required in relatively high levels in order to provide a sufficient anti-block effect. However, at such higher levels, the anti-block agent can negatively impact the mechanical properties of the product for a given application, e.g., the modulus is too high or the tear and tensile strength are too low. This change in properties usually becomes unacceptable when such anti-block agents are used at a level of over about 5–10 weight % of the composition. In addition, it may be desired to avoid the use of an anti-block agent where the agent is not environmentally inert or biodegradable, where the agent is potentially toxic to humans, or where the agent interferes significantly with heat sealing properties or other properties of the polymeric product.

The set time is influenced by the polymer material and the processing equipment and conditions. In general, the set time should be on the order of seconds under conventional process conditions. Such conditions typically include temperatures ranging from that of chill rolls, such as are known in the art, to the melt temperature of the material being processed, which may be up to about 600° C. In general, longer process cycle times (e.g., from the point of melt extrusion to the point of take-up or collection) tend to accommodate longer set times. For example, cast film processes tend to accommodate compositions having a relatively long set time, as compared to blown film processes.

For semi-crystalline polymers, the set time depends on the rate of crystallization of the polymer or on the glass transition temperature (i.e., $T_g$) of the polymer. For amorphous polymers, the set time depends on the glass transition temperature of the polymer. In general, if the $T_g$ is above the temperature of the polymer during the later stages of shaping, the set time is virtually immediate as a result of vitrefication. For semicrystalline polymers with a $T_g$ below the temperature at the time of shaping, a suitable set time is generally achieved where the radial growth rate is at least about 1 micron per second. The radial growth rate is the rate at which the radius of a growing spherulite increases with time. A spherulite is a spherical aggregate composed of crystalline lamellae ranging in size from submicroscopic to a diameter on the order of millimeters.

Polymers that tend to be difficult to melt process are exemplified by polycaprolactone, and thermoplastic polyurethanes having a $T_g$ below the temperatures typically employed in melt shaping. Such polymers are primarily limited by their relatively long set times at typical melt process conditions. Other polymers that tend to be difficult to melt process are polyhydroxy alkanoates, for example, polyhydroxybutyrate and polyhydroxybutyrate/valerate copolymers. Such polymers are primarily limited by their relatively low melt strength.

Yet other biodegradable polymers possess many or all of the physical properties desired for certain applications, such as in disposable absorbent articles, but are less suitable for use in products that are to be composted. This is because the polymers do not degrade fast enough to break up into small fragments in the early stages of composting. Hence, there is a strong likelihood that such polymers would be screened out of the compost stream and not become part of the final compost. Several of such polymers have a melt point or $T_g$ that is above the temperatures typically encountered in commercial composting units, e.g., above about 65° C. Examples of such polymers include hydrolytically cleavable polyesters. Hydrolytically cleavable polyesters suitable for use herein are polyesters that are cleaved to low molecular weight, biodegradable fragments via reaction with water or water at acid or basic pH, particularly at temperatures above 65° C. Polymers of this type include the aromatic/aliphatic polyester copolymers described herein, oxidized ethylene/carbon monoxide copolymers, and aliphatic polyesters with melting points or glass transition temperatures above about 65° C. such as those described herein.

Polymers which are useful in forming the compositions of the present invention can be classified as follows. It will be understood by the skilled artisan that certain polymers may be classified in more than one group.

A. MOISTURE SENSITIVE POLYMERS

One type of moisture sensitive polymer suitable for use herein are the compositions based on destructurized starch interpenetrating networks (alternatively referred to herein as "starch IPNs"). Thermoplastic, biodegradable compositions based on interpenetrated networks of starch with a synthetic component such as an ethylene/vinyl alcohol (EVOH) copolymer are described in International Patent Applications WO 90/10671, WO 90/110069.3, WO 91/02025, WO 91/02024, WO 91/02023, European Patent Application No. 90810533.1, and U.S. Pat. No. 5,095,054; all herein incorporated by reference. Such materials are available commercially from Novamont under the tradename Mater-Bi, for example, the commercially available material codes AF05H and AF010H, and from Warner Lambert under the tradename Novon. These materials contain greater than 50% starch by weight and are therefore very sensitive to moisture vapor levels in the ambient atmosphere as well as direct contact with liquid water.

Films formed of only the interpenetrated network of starch and a synthetic component can be extruded with very good mechanical properties initially. However, these properties vary considerably with humidity. For example, the modulus of a Mater-Bi film (Type AF05H) decreases by about 50% as the relative humidity changes from about 20% to 90%. Although such sensitivity to humidity is a reversible process, it makes the film inconsistent on a day-to-day basis to the degree that converting operations and end use performance are negatively affected.

Mater-Bi films also absorb water to a high degree, typically about 30% of their initial weight. In addition to lowering the strength of the film significantly, the high water absorption also leads to very high moisture transmission through the film, for example, about 0.0024 grams/cm²/16 hours through a 30 micron film. This is beneficial in some applications where breathability is desired. However, high moisture transmission may not be desirable if the film is expected to contain large quantities of fluids, as in the case of a diaper backsheet. High water permeation can lead to excessive condensation on the outside of the backsheet, leaving it cold and wet feeling to the touch.

Novon films can also be extruded with good initial properties. Some, however, like Novon grade M0014 are so sensitive to water they quickly fall apart, disperse into smaller particles, and virtually dissolve when contacted or immersed in liquid water.

Another type of moisture sensitive polymer that is useful herein is polyvinyl alcohol (hereinafter alternatively referred to as PVA(s)) and derivatives thereof. Chemically, PVA can be described as a polyhydric alcohol with hydroxyl groups extending from alternate carbon atoms. It is represented structurally as having the following repeating units:

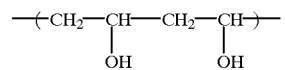

PVA is prepared via hydrolysis of polyvinylacetate. Depending on the degree of hydrolysis, PVA can be obtained in grades which are soluble in both cold and hot water or hot water only. PVOH is commercially available from Hoechst Celanese Corp. under the tradename MOWIOL.

The biodegradability of PVA is well documented. A brief overview on its biodegradation can be found in *Handbook of Water-Soluble Gums and Resins*, R. L. Davidson, Editor; Chapter 20, p. 20–17 (McGraw Hill 1980), herein incorporated by reference.

Unmodified PVA is not thermoplastic. However, when PVA is plasticized with appropriate additives, thermoplastic materials can be obtained. PVA can be plasticized either externally by blending PVA with a suitable plasticizer, or internally, for example, by copolymerizing PVA with a suitable plasticizing copolymer.

External plasticizers include glycerol, ethylene glycol, and low molecular weight polyethylene glycols, for example, polyethylene glycols having a number average molecular weight of from about 200 to about 1500 grams/mole. Certain grades of MOWIOL polyvinyl alcohol may be externally plasticized. Hoechst Celanese Corp. technical brochure G-CS1103E/1092 entitled "MOWIOL Polyvinyl Alcohol," incorporated herein by reference, describes in detail the external plasticizers that are generally used with the MOWIOL resins, and the mixing procedure that should be followed. Once plasticized, any of the MOWIOL grades can be employed in the compositions of the present invention. The 18–88, 26–88 and 30–92 grades, which are described in the above-referenced brochure, are preferred since they are relatively high molecular weight materials suitable for film and fiber applications.

Internally plasticized, thermoplastic PVA compositions suitable for use herein, and particularly as components for the films of the present invention, are sold by Air Products and Chemicals, Inc. of Allentown, Pa., under the tradename Vinex. Vinex resins are internally plasticized compositions achieved by copolymerizing PVA with a poly(alkyleneoxy) acrylate. More detailed disclosures of these materials are given in U.S. Pat. Nos. 4,618,648 and 4,675,360; both herein incorporated by reference. Still another method for making internally plasticized, thermoplastic polyvinylalcohol compositions via the incorporation of polyurethanes is disclosed in U.S. Pat. No. 5,028,648, herein incorporated by reference. The biodegradation of Vinex compositions is disclosed in an Air Products Technical Bulletin entitled "Measurement of the Biodegradability of Vinex Resins by Controlled Respirometry" by J. Kramer, herein incorporated by reference. A Vinex 2000 series exists, and is especially preferred for use in film forming compositions. Such materials, for example, Vinex 2034 and Vinex 2144, form tough, tear resistant films which, if not for their water solubility, would meet the mechanical strength requirements for biodegradable backsheets of absorbent articles. Vinex 2019 is another polymer grade that is suitable for use herein. The 2019 has a lower molecular weight and a lower processing temperature than the Vinex 2144 and 2034 (160° C. for the 2019 grade versus 190° C. for the 2034 and 2144 grades). The Vinex 2019 may be used to minimize the thermal degradation of the other components of the polymer composition, particularly polyhydroxyalkanoates where these are used. Internally plasticized polyvinyl alcohol compositions are also available from the Hoechst Celanese Corp., for example, under the tradename MOWIOL.

Another moisture sensitive polymer that may be used herein is hydroxypropyl cellulose (alternatively referred to herein as HPC(s)). HPC is a non-ionic cellulose ether with an unusual combination of properties among cellulose derivatives. These include solubility in both water and polar organic solvents as well as plastic flow properties that permit its use for molded and extruded articles such as films. As described in the aforementioned *Handbook of Water Soluble Gums and Resins*, Chapter 13, herein incorporated by reference, the plastic flow properties of HPC enable it to be used as a base material in extrusion, blow, or injection molding, and film-making operations. Thermally processed products formed by these methods retain their water solubilities, are biodegradable, and can even be made to be edible.

The chemical cellulose used to prepare HPC is derived from wood pulp or cotton linters. The cellulose is treated with aqueous sodium hydroxide to form alkali cellulose which, in turn, is reacted with propylene oxide to yield the following empirical structure:

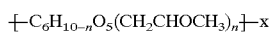

where n has a range of 3 to 4.5 and x has a range of 150 to 3000. Commercially, HPC is available from Hercules Inc. under the tradename KLUCEL.

B. THERMALLY SENSITIVE POLYMERS

Thermally sensitive polymers suitable for use herein include certain linear, saturated (i.e., aliphatic) polyesters. Many thermally sensitive, aliphatic polyesters are known to be biodegradable and compostable. Although some types of thermally sensitive, aliphatic polyesters can be melt processed directly into various products, their melting points or softening points are too low to allow their use alone in many applications. For example, thermally sensitive, aliphatic polyesters are not singularly suitable for forming a monolayer backsheet for disposable absorbent articles.

Polycaprolactone (alternatively referred to herein as PCL (s)) is an example of a preferred biodegradable, aliphatic polyester for use in the present invention. It can be produced via the ring opening polymerization of epsilon-caprolactone, a seven-membered ring compound. As described in Union Carbide Brochure F-60456 entitled "Tone Polymers," herein incorporated by reference, the polymerization is initiated with a diol (HO-R-OH, where R is an aliphatic segment) to produce polymers with the following structure:

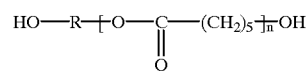

where n is the degree of polymerization.

Polycaprolactone polymers are available from Union Carbide Corporation under the tradename TONE in a variety of molecular weight grades. For example, TONE polymers P-300 and P-700 have degrees of polymerization of about 95 and 400 respectively, corresponding to number average molecular weights of about 10,000 and 40,000 grams/mole. TONE P-767 is prepared from a special high purity grade of caprolactone monomer and has a number average molecular weight of about 43,000 grams/mole. TONE P-787 has a degree of polymerization of about 700 and an even higher number average molecular weight of about 80,000 grams/mole.

For use in the films of the present invention, polycaprolactone polymers having a number average molecular weight of 40,000 or more are preferred. Especially preferred are polycaprolactone polymers having a number average molecular weight of about 80,000 grams per mole (e.g., TONE P-787).

Polycaprolactone polymers having number average molecular weights of about 40,000 grams/mole and greater can be melt processed into strong, water resistant films. Except for their low melting point of about 60° C. (140° F.), these films could function as backsheets for absorbent articles. Because of their low melting points, backsheets consisting of 100% polycaprolactone are difficult to stabilize in storage environments approaching temperatures of about 60° C., and would have difficulty withstanding the high temperatures that may be encountered during disposable absorbent article fabrication.

Other types of thermally sensitive, aliphatic polyesters suitable for use in the compositions of the present invention are those derived from the reaction of an aliphatic dicarboxylic acid and a diol. As described in "An Overview of Plastics Degradability," Klemchuk, *Modern Plastics* (August 1989); incorporated herein by reference, many of these polyesters are biodegradable since they are susceptible to enzymatic hydrolysis.

Moreover, the acid and alcohol fragments of the hydrolysis are also easily assimilated by microorganisms.

Such polyesters are prepared via the generalized reaction shown below:

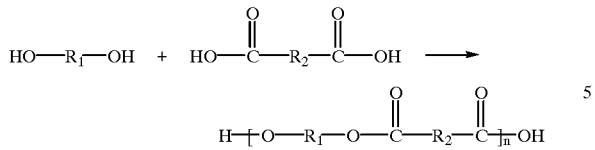

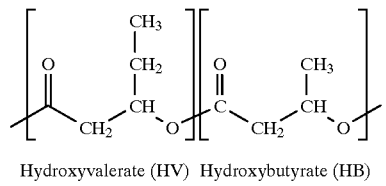

Hydroxyvalerate (HV) Hydroxybutyrate (HB)

where $R_1$ is a linear methylene chain $-(CH2-)_x$ with $2<x<10$, $R_2$ is also a linear methylene chain $-(CH2-)_y$ with $2<y<10$; and n is the degree of polymerization. Examples of these types of aliphatic polyesters include:

Polyethylene adipate where x=2 and y=4; Tm (i.e., melt point temperature)=50° C.

Poly (1,3 propanediol adipate) where x=3 and y=4; Tm=38° C.

Poly (1,4 butanediol adipate) where x=4 and y=4; Tm=48° C.

Poly (1,4 butanediol sebacate) where x=4 and y=8; Tm=64° C.

Poly (1,3 propanediol succinate) where x=3 and y=2; Tm=47° C.

Poly (1,4 butanediol glutarate) where x=4 and y=3; Tm=47° C.

Further examples of thermally sensitive, aliphatic polyesters can be found in *Polymer Handbook*, Third Edition, J. Brandrup and E. H. Immergut, John Wiley & Sons (1989), Section VI, pages 56–67, herein incorporated by is reference.

C. POLYMERS DIFFICULT TO MELT PROCESS

Poly (hydroxy alkanoates) (alternatively referred to herein as PHA(s)) form one class of polymers that are difficult to process by melt methods. Poly (hydroxy alkanoates) can be synthetically derived from hydroxy carboxylic acids. This class of polymer also includes naturally derived polymers such as polyhydroxybutyrate (PHB), including homopolymers of 3-hydroxybutyrate and 4-hydroxybutyrate. Other PHAs include copolymers of PHB with hydroxy acids, for example, copolymers of PHB with 3-hydroxypropionate, 3-hydroxyvalerate, 3-hydroxyhexanoate, 3-hydroxyoctanoate, or longer chain hydroxy acids (e.g., $C_9$–$C_{12}$ hydroxy acids) and copolymers thereof. The PHA can be predominantly of R(−) configuration, predominantly of S(+) configuration, or a random, block, or other combination of R(−) and S(+) configuration. As will be understood by the skilled artisan, the R(−) and S(+) isomers refer to the ability of the repeat unit of the polymer to rotate plane polarized light in the counterclockwise or clockwise direction, respectively. A racemic copolymer consists of both R(−) and S(+) repeat units within the polymer which can be arranged in any combination, including random or block configurations.

Preferred examples of polyhydroxybutyrate homopolymer and polyhydroxybutyrate/valerate copolymers are described in U.S. Pat. No. 4,393,167, Holmes et al., issued Jul. 12, 1983, and U.S. Pat. No. 4,880,592, Martini et al., issued Nov. 14, 1989, both references incorporated herein by reference. PHBV copolymers have the generalized structure shown below.

Such copolymers are commercially available from Zeneca Bioproducts of New Castle, Del., under the tradename Biopol. The Biopol polymers are produced from the fermentation of sugar by the bacterium Alcaligenes eutrophus. PHBV polymers are have been produced with valerate contents ranging from about 5 to about 95 mol %, and are currently commercially available with valerate contents ranging from about 5 to about 12 mol %. Increasing valerate content decreases the melting point, crystallinity, and stiffness of the polymer. An overview of Biopol technology is provided in Business 2000+ (Winter 1990), incorporated herein by reference.

Other examples of copolymers of PHB and other hydroxy acids, e.g., $C_6$–$C_{12}$ hydroxy acids, are described in copending U.S. patent application Ser. No. 08/189,015, filed Jan. 28, 1994; copending U.S. patent application Ser. No. 08/189,029, filed Jan. 28, 1994; copending U.S. patent application Ser. No. 08/188,271, filed Jan. 28, 1994; and copending U.S. patent Application Ser. No. 08/247,539, filed May 23, 1994. The disclosures of each of these patent applications are incorporated herein by reference in their entirety. Other polymers that are suitable for use herein are described by E. Shimamura, et al., *Macromolecules*, 27, 4429 (1994), incorporated herein by reference. Shimamura et al. describe isotactic homopolymers and copolymers of (R)-3-hydroxyalkanoic acids with four to fourteen carbon atoms, having saturated, unsaturated, halogenated, branched, and aromatic side chains in the 3-hydroxyalkanoic acid monomeric unit. This reference also describes copolymers containing hydroxyalkanoate monomeric units without side chains, such as 3-hydroxypropionate, 4-hydroxybutyrate, and 5-hydroxyvalerate. Polyhydroxyalkanoates that are suitable for use herein are also described in International Publication No. WO 94/00506, incorporated herein by reference.

Polyhydroxyalkanoates tend to exhibit thermomechanical integrity over the temperatures that may be typically encountered during converting processes of disposable absorbent articles, as previously described in reference to backsheet films. Unfortunately, polyhydroxyalkanoates tend to have low melt strengths and may also suffer from a long set time, such that they tend to be difficult to melt process. PHA also tends to suffer from thermal degradation at very high temperatures such as may be encountered during melt processing. In addition, unmodified PHA, and especially PHB and PHBV, may be stiff and brittle, i.e., they have a relatively high tensile modulus (typically greater than about 1000 MPa) and a relatively low elongation at break (typically less than about 10%). PHAs formed from hydroxy acids containing at least 6 C atoms are generally preferred for their mechanical properties. However, the set time tends to increase with an increasing C number. Therefore, the particular PHA will be selected as needed for a given application and processing method.

Polycaprolactone and some polyurethanes may also be considered to be difficult to melt process. However, the primary limitations associated with these polymers are, respectively, their thermal sensitivity and mechanical limitations.

D. MECHANICALLY LIMITED POLYMERS

One type of mechanically limited polymer that is suitable for use herein are cellulose esters and plasticized derivatives thereof. Cellulose esters are produced by the chemical modification of cellulose and include the family of cellulose acetates, cellulose acetate propionates, and cellulose acetate butyrates (hereinafter alternatively referred to as CA(s), CAP(s), and CAB(s), respectively). As described in *Modern Plastics Encyclopedia*, pp. 23–24 (McGraw-Hill 1990), herein incorporated by reference, cellulose esters are prepared by reacting cellulose with particular acids and acid anhydrides, generally in the presence of a sulfuric acid catalyst. In the case of CA, the reaction is first carried out with acetic acid and acetic anhydride to produce cellulose triacetate, which contains nearly 100% acetyl substitution or, in other words, a degree of substitution of about 3.0. The triacetate is then partially hydrolyzed to remove some of the acetyl groups such that the CA product contains about 38 to 50% acetyl substitution.

CAP and CAB are made by substituting propionic acid and propionic anhydride or butyric acid or butyric anhydride for some of the acetic acid and acetic anhydride. Plastic grades of CAP generally contain 39 to 47% propionyl and 2 to 9% acetyl content. Plastic CAB grades generally contain 26 to 39% butyryl and 12 to 15% acetyl content. Commercially, CA, CAB, and CAP are obtained from Eastman Chemical Co., Inc., of Kingsport, Tenn., under the tradename Tenite.

Fully formulated grades of cellulose esters may also contain plasticizers, heat stabilizers, and ultraviolet inhibitors. High levels of these stabilizers and inhibitors may further slow the rate of biodegradation of cellulose esters. Zero or very low levels of such stabilizers are generally preferred in films which are desired to be biodegradable.

Although raw cellulose and its regenerated film (cellophane) and fiber (rayon) forms are readily biodegradable, the esterification of cellulose can make it quite stable to microbial attack. As described in *Polymer Degradation*, W. Schnabel (Macmillan 1981), herein incorporated by reference, this enhanced resistance to biodegradation results from the inability of cellulose-specific enzymes to attack the substituted portions of the polysaccharide. However, as described by Buchanan, Gardner and Komarek, in a paper entitled "The Fate of Cellulose Esters in the Environment: Aerobic Biodegradation of Cellulose Acetate," *J. Applied Polymer Sci.*, 47, 1709 (1993), the rate of degradation of cellulose esters also depends upon the degree of substitution. In general, the biodegradable cellulose esters herein have a degree of substitution of less than 2.5, preferably less than 2.0. For example, a CA with a 1.7 degree of substitution was found to biodegrade much faster than a CA with a 2.5 degree of substitution. Plasticized CA with a degree of substitution between 1.7 and 2.5 provides a suitable balance between melt processability and biodegradability, and are therefore the preferred cellulose esters for use herein. As reported by J. D. Gu, et al., *J. Environ. Polym. Degradation*, 1, 143, (1993), CA having a degree of substitution greater than 2.5 were not biodegradable. CA having a degree of substitution less than 1.7 are generally not melt processable, even with the addition of a plasticizer.

Plasticized cellulose esters, such as CA, CAP, and CAB are thermoplastic and can be melt processed into thin films and other products. Unless substantial levels of plasticizer are employed, the stiffness of such films is too high for them to be useful in applications requiring flexibility, such as backsheets for absorbent articles. Even in the presence of plasticizers, the tear propagation resistance of cellulose ester films is too low for such applications, typically below 10–15 grams per 25.4 microns of thickness in the machine direction.

Some blends of cellulose esters, and plasticized derivatives thereof, with aliphatic polyesters can form another type of mechanically limited polymer that is useful herein. It is well known that cellulose esters form miscible blends with many aliphatic polyesters. U.S. Pat. No. 3,642,507, herein incorporated by reference, discloses the formulation of printing inks with improved flexibility by blending a cellulose ester with polycaprolactone. U.S. Pat. No. 3,922,239, herein incorporated by reference, also discloses the preparation of thermoplastic blends of cellulose esters and polycaprolactone and other cyclic ester polymers. The addition of the polyesters was found to lower the modulus of the blend significantly below that of the cellulose ester and to impart improved melt processability, toughness, and impact resistance.

More recently, blends of CAP and CAB with polyhydroxybutyrate (PHB) have been described in several papers: "Miscibility of Bacterial Poly(3-hydroxybutyrate with Cellulose Esters," Scandola et al., *Macromolecules*, 25, 6441 (1992); "Cellulose Acetate Butyrate and Poly (hydroxybutyrate-co-valerate) Copolymer Blends," Buchanan et al., *Macromolecules*, 25, 7373 (1992); and "Miscibility of Bacterial Poly(3-Hydroxybutyrate-co-3-hydroxyvalerate) with Ester Substituted Celluloses," Lotti et al., *Polymer Bulletin*, 29, 407 (1992); each being incorporated herein by reference. Experimental evidence of miscibility was found up to 50% PHB. Crystallization of the PHB was found to be strongly inhibited by the presence of cellulose esters confirming intimate mixing of the blend components. Similar results are obtained if PHBV copolymers are employed in place of PHB.

Blends as described above are thermoplastic and may, depending on the specific blend, be processed into thin, flexible films with stiffness levels appropriate for backsheet films. However, the tear propagation resistance, tensile elongation, or thermomechanical integrity of such films alone is still deficient compared to those normally used to construct many products, including absorbent articles such as disposable diapers. As will be discussed later, the inclusion of certain biodegradable elastomers can improve the tear strength of such blends significantly. In addition, these materials may suffer from relatively long set times, which can make melt processing difficult.

Another polymer that can be classified as being mechanically limited is polylactide (alternatively referred to herein as PLA(s)). PLA is a semicrystalline polymer having a relatively high melt point ranging from about 100 to about 130° C., depending on the degree of crystallinity which in turn depends on the relative amounts of the R(+) and S(−) enantiomers in the polymer. The homopolymer tends to be more useful for fiber and nonwoven applications than for film applications. This is because the polymer, having a glass transition temperature of about 65° C., tends to form films of the polymer which are stiff and brittle. Although these limitations can be reduced by adding a plasticizer, the plasticizer level typically required for a significant influence (at least about 20 weight %) tends to excessively reduce the melt strength of the polymer such that extrusion processing is difficult. In addition, such plasticized films tend to have a greasy feel.

PHB and PHBV copolymers may also be considered to be mechanically limited, since films of the copolymer tend to be brittle. However, the primary limitation associated with these copolymers is the difficulty in forming products of the copolymer by melt processes. Some aliphatic polyester-based polyurethanes may also be considered to be mechanically limited due to a relatively low tensile modulus, e.g., on the order of less than about 70 MPa.

E. HYDROLYTICALLY CLEAVABLE POLYESTERS

Aromatic/aliphatic polyester copolymers form one type of hydrolytically cleavable polyester suitable for use in the present invention. These polymers are generally derived from aromatic polyesters such as polyethylene terephthalate (PET) and polybutylene terephthalate (PBT). Although neither PET or PBT are considered to be biodegradable polymers, several means of making such aromatic polyesters more readily hydrolytically cleavable, and hence more likely to be biodegradable, have recently been described. U.S. Pat. No. 5,053,482 issued to Tietz on Oct. 1, 1991, describes polyesters based on polyethylene terephthalate (PET) copolymerized with diethylene glycol and 5-sulfoisophthalic acid wherein the glass transition temperature of the copolymers is preferably reduced to below 65° C., within the range of normal composting operations. Although hydrolysis of the films and fibers of the copolymer is shown to take place in boiling water (100° C.), evidence of the extent or rate to which true biodegradation occurs is not presented.

Yet another approach to increasing the hydrodegradability of aromatic polyesters is described in International Patent Application WO 91/02015, published Feb. 21, 1991, herein incorporated by reference. This publication discloses hydrodegradable polyesters based on the random copolymerization of aromatic and aliphatic polyesters. More specifically, the random copolymers are derived from aromatic polyesters such as PET or PBT randomly interrupted with aliphatic hydrodegradable link polymers such as polyglycolic acid, polylactic acid, polycaprolactone, polyhydroxybutyrate, polyhydroxybutyrate/valerate, polybutylene oxalate, polyethylene adipate, polyethylene carbonate, polybutylene carbonate, and other polyesters containing silyl ethers, acetals, or ketals. Preparation of the copolymers is carried out by either ester interchange reactions of the appropriate monomeric species or by transesterification reactions between two homopolymers in the presence of an appropriate catalyst.

In addition to the aforementioned aliphatic link polymers, other aliphatic polyesters may also be appropriate for producing aromatic/aliphatic polyester copolymers. These include aliphatic polyesters selected from the group of oxalates, malonates, succinates, glutarates, adipates, pimelates, suberates, azelates, sebacates, nonanedioates, and mixtures thereof.

For the polymers described in Tietz and WO 91/02015, it is assumed that true biodegradation will occur once the copolymers hydrolyze to very low molecular weight oligomers or monomeric species. However, it is believed that the rate of biodegradation will be significantly slower than other biodegradable polymers described herein, even in typical composting environments. In addition, it is believed that the ability of these polymers to break up into smaller fragments which are able pass through typical, commercial composting processes will be significantly less than such other polymers. The incorporation of other, more rapidly biodegradable polymers as described herein, tends to enhance the initial breakup and ultimate degradation of such polyester copolymers.

Another type of hydrolytically cleavable polyester that may be used in the present invention includes oxidized ethylene-carbon monoxide copolymers. Copolymers of ethylene and carbon monoxide are disclosed in U.S. Pat. No. 2,495,286 issued to Brubaker, herein incorporated by reference. It has been found that such ethylene/carbon monoxide polymers can be oxidized to yield aliphatic polyesters that are hydrolytically degradable. Polymers of this type are described in U.S. Pat. No. 4,929,711, herein incorporated by reference. This patent describes a process for converting a polyketone, for example an ethylene/carbon monoxide (herein alternatively referred to as ECO) copolymer, to a polyester. The process involves the reaction of the ECO copolymer with an organic peroxyacid oxidizing agent in an inert liquid medium at temperatures between –20° C. to 150° C. Substantially all or only a portion of the ketone functionality can be converted to ester groups depending upon the reaction conditions.

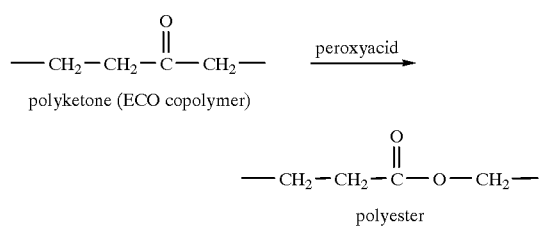

U.S. Pat. No. 4,957,997 extends this process to polyketones containing pendant functional groups obtained by the copolymerization of carbon monoxide with vinyl or vinylidene monomers. The vinyl or vinylidene monomer may have at least one functional group containing one or more oxygen, nitrogen, sulfur, or halogen atoms.

The polyesters described in these patents may originate from polyketones containing 0.5 to 20 weight percent carbon dioxide and having a number average molecular weight of from about 10,000 to about 1,000,000 grams per mole. After oxidation to the corresponding polyesters, the materials are capable of being hydrolyzed to lower molecular weight fragments. The rate and extent to which both hydrolytic and microbial degradation occur depend on the number of ester groups present and the number average molecular weight of the polymer between ester groups. The lower the molecular weight fragments resulting from hydrolysis become, the more susceptible they become to microbial attack and biodegradation. For purposes of biodegradation and compostability, the number average molecular weight of the polymer chains between ester groups is preferably below 1000 grams per mole, most preferably below about 500 grams per mole.

Yet another family of hydrolytically cleavable and biodegradable polyesters includes high melting aliphatic polyesters defined, herein, as those having glass transition temperatures or melting points above 65° C. Such materials may not undergo initial decomposition and breakup during the early stages of typical, commercial composting processes since the crystalline fraction, the amorphous fraction, or both the crystalline and amorphous fractions of these materials may be below their melting points or glass transition temperatures at normal composting temperatures. According to the present invention, high melting aliphatic polyesters can be combined in blends with other, more rapidly degrading materials, for example, moisture sensitive or thermally sensitive polymers, to enhance their rates of initial decomposition and breakup. Suitable blends are described herein.

Examples of high melting aliphatic polyesters include polyethylene sebacate (Melting temperature, i.e., Tm=76° C.), polyethylene succinate (Tm=108° C.), and polyhexamethylene sebacate (Tm=78° C.). Further examples can be found in the aforementioned *Polymer Handbook, Third Edition*, Section VI, pages 56–67, previously incorporated herein by reference.

F. ELASTOMERS

As defined herein, a thermoplastic elastomer (alternatively referred to herein as TPE(s)) is a material that combines the processability of a thermoplastic with the functional performance and properties of a conventional thermosetting elastomer as discussed in *Modern Plastics Encyclopedia*, pp. 122–131 (McGraw-Hill 1990), herein incorporated by reference. Commercially, there are 6 generic classes of TPE: styrenic block copolymers, polyolefin blends, elastomeric alloys, thermoplastic polyurethanes, thermoplastic copolyesters, and thermoplastic polyamides. For use in the products of the present invention, the thermoplastic elastomer must be biodegradable. From the aforementioned list of TPE classes, only a select group of thermoplastic polyurethanes, specifically aliphatic polyester-based polyurethanes, are generally recognized as being biodegradable.

Biodegradable polyurethanes can be prepared from low molecular weight aliphatic polyesters derived from epsilon-caprolactone or the reaction products of a diol-dicarboxylic acid condensation. In general, these low molecular weight polyesters have number average molecular weights of less than 10,000 grams per mole and frequently as low as 1,000 to 2,000 grams per mole. Examples of biodegradable polyester urethanes derived from polyethyleneglycol adipate, poly (1,3-propanediol adipate) and poly (1,4-butanediol adipate) are disclosed in "The Prospects for Biodegradable Plastics," F. Rodriguez, *Chem Tech* (July 1971), incorporated herein by reference. Aliphatic polyester urethanes suitable for use herein are available from Morton International, Inc. under the tradename Morthane. For example, Morthane PN03–204 and Morthane PN3429-100 have been found suitable for use herein. Morthane PN03-04 and Morthane PN3429-100 have a number average molecular weight, respectively, of 96,000 grams/mole and 120,000 grams/mole. It has been found that, in the compositions of the present invention, PN03-204 tends to be more compatible, while PN03-204 tends to be a better processing aid.

In general, as the number average molecular weight and the hard/soft segment ratio of the polyurethane decreases, the polymers of the blend containing the polyurethane tend to be more compatible. As the number average molecular weight and the hard/soft segment ratio of the polyurethane increases, the blend containing the polyurethane tends to exhibit better processing, which is believed to be due to an enhancement of the melt strength. The polyurethane may be selected within these guidelines by the skilled artisan to leverage the attributes of the particular urethane as necessary.

Another type of TPE that is suitable for use in the compositions herein are the block copolymers of polycaprolactone with polydienes. Copolymers of this type are disclosed in U.S. Pat. No. 3,585,257 issued to Mueller et al., herein incorporated by reference. This patent discloses block copolymers of polycaprolactone with polydienes such as polyisoprene and polybutadiene in which the polycaprolactone content can be varied from about 20 to about 80 weight percent and the diene content varied from about 80 to about 20 weight percent. Copolymers having tensile strengths in the range of between 245 and 2,000 pounds per square inch and elongations to break in the range from 400 to 560 percent are obtained.

The polycaprolactone/polydiene block copolymers can be prepared having various architectures. For example, an A-B diblock copolymer has a block of polymer A segments coupled to a block of B polymer segments. An A-B-A triblock copolymer has a block of B segments coupled to a block of A segments at each of its terminal ends. An—(A-B)$_n$—multiblock copolymer has alternating sequences of A and B segments where n is a positive integer greater than 1.

For toughening and increasing the tear strengths of films of the present invention, A-B-A triblock or—(A-B)$_n$—multiblock copolymers in which the A blocks include polycaprolactone, and n is a positive integer greater than 1, are generally preferred. Simple diblock A-B copolymers do not impart significant tear strength improvement to films of the present invention. Especially preferred are triblock copolymers in which the polycaprolactone segments comprise from about 10 to about 60 weight percent of the copolymer and the polydiene segments comprise from about 90 to about 40 weight percent of the copolymer.

COMPOSITIONS OF THE PRESENT INVENTION

The compositions of the present invention are derived from blends of various biodegradable polymers, selected and compounded such that the deficiencies of the individual, polymeric components as previously described are overcome. Thus, the compositions include at least two polymers which suffer from different primary limitations such as previously described.

The compositions contain compatible or semicompatible blends of polymers. As is understood by those skilled in the art, compatible blends typically exhibit synergistic behavior in at least one mechanical property, as compared to the individual polymers in the blend. Other mechanical properties are typically intermediate those of the individual polymers. Semicompatible polymers typically exhibit mechanical properties that are between those of the individual polymers making up the blend. In contrast, incompatible blends typically exhibit phase separation on a macroscale (i.e., on the order of microns) and at least one mechanical property, generally substantially all mechanical properties, which is diminished relative to each of the individual polymers making up the blend. Incompatible blends often have relatively low strengths and low elongations to break.

The compositions of the present invention are thermoplastic and can be melt processed into biodegradable products, such as fibers and films, having physical integrity. Products formed from preferred compositions exhibit thermomechanical integrity and mechanical properties that enable their use in a number of practical applications. For example, certain preferred compositions are suitable for application in disposable absorbent articles, e.g., as a topsheet or backsheet material.

The compositions may be described as being a blend of two or more polymers selected from the categories of moisture sensitive polymers, thermally sensitive polymers, mechanically limited polymers, polymers difficult to melt process, hydrolytically cleavable aromatic/aliphatic polyester copolymers, oxidized ethylene/carbon monoxide copolymers, high melting aliphatic polyesters, and biodegradable elastomers. The following general conditions apply to the compositions of the present invention.

When used, a moisture sensitive polymer is typically used in an amount of from about 1% to about 50% by weight of the composition. As the skilled artisan will understand, the moisture sensitivity of the composition tends to increase as the amount of moisture sensitive polymer increases. The amount of moisture sensitive polymer will therefore generally be selected to provide an acceptable moisture resistance, e.g., an acceptable moisture transport rate, for a given application. For liquid impervious film and other applications, the moisture sensitive polymer will generally be used in an amount of from about 1 to about 40 percent, more preferably from about 1 to about 30 percent, based on the total weight of the biodegradable polymers in the composition.

Preferred moisture sensitive polymers for use in the present invention are thermoplastic polyvinyl alcohol compositions and the starch IPNs. These materials are particularly useful for imparting good melt processing (by increasing melt strength and reducing set time) and tensile properties which are generally suitable for film and fiber applications.

The moisture sensitive polymers classified as thermoplastic polyvinyl alcohol compositions and starch IPNs tend to be compatible with the aliphatic polyester-based polyurethanes and polycaprolactone used herein, but incompatible with polylactides, cellulose esters, hydroxypropyl cellulose, and polyhydroxyalkanoates.

It has been found that polycaprolactone and aliphatic polyester-based polyurethanes can compatibilize a mixture including a thermoplastic polyvinyl alcohol composition and/or starch IPN, and one or more of a polylactide, cellulose ester, hydroxypropyl cellulose, or polyhydroxyalkanoate. This compatibilization can occur when the combined amount of polycaprolactone and/or polyurethane exceeds the combined amount of the polylactide, cellulose ester, hydroxypropyl cellulose, and polyhydroxyalkanoate. Thus, compatibilization can occur when the weight ratio of PCL and polyurethane to these latter polymers is at least about 1:1. In such case, the level of the moisture sensitive polymer is generally dictated by end use considerations.

If the aforementioned weight ratio is less than about 1:1, the moisture sensitive polymer is employed at levels which tend to minimize the negative influence of any phase separation which may occur, yet which provides a benefit to the composition, for example, good melt processing. In such cases, up to about 10 weight % of the moisture sensitive polymer will be used, based on the total weight of the biodegradable polymers in the composition.

When employed in the compositions of the present invention, thermally sensitive polymers tend to increase the rate of biodegradation or to enhance fragmentation of products when the product is exposed to temperatures above about 60° C., such as typically occurs in commercial composters. The thermally sensitive polymer typically makes up from about 5 to about 80, preferably from about 20 to about 80, weight percent of the blend, based on the total weight of the biodegradable polymers in the blend.

Preferred polymers which tend to be thermally sensitive are polycaprolactone and aliphatic polyester-based polyurethanes. These materials impart flexibility and strength to the polymeric product and have been found to be compatible with other polymers. In general, polycaprolactone is preferred when improvements in tensile and tear strength are of greatest importance; while polyurethane is preferred when increases in flexibility (evidenced by a decrease in modulus) are desired. The skilled artisan will be able to select appropriate levels of these polymers in light of the teachings herein in order to achieve a suitable balance of strength and flexibility. Typically, a total of at least about 20 weight % of polycaprolactone and/or polyurethane is needed to measurably affect the mechanical properties of the product, and usually not more than about 60 weight % total is used so as to not restrict the effective upper temperature use to about 60° C. However, in compositions including blends of polyhydroxyalkanoates, as much as 80 weight % polycaprolactone and/or polyurethane can be used as further described herein.

Polyhydroxyalkanoates are exemplary polymers that are difficult to melt process. Polyhydroxyalkanoates tend to be compatible with other polymers, e.g., the thermally sensitive polymers, mechanically limited polymers, high melting polyesters, and the hydrolytically cleavable copolyesters described herein, with the exception of moisture sensitive polymers such as those described herein. It has been found, however, that the thermally sensitive polymer polycaprolactone and aliphatic polyester-based polyurethane polymers can be used to compatibilize a polyhydroxyalkanoate and a moisture sensitive polymer, as described herein.

Compositions including a polyhydroxyalkanoate tend to possess the beneficial thermomechanical properties of the polyhydroxyalkanoate, while avoiding the processing difficulties which are associated with that polymer type. Other polymers having a relatively high melting point or glass transition temperature may also be used to impart thermomechanical integrity to the composition. For compositions to be used in backsheet films, such other polymers will preferably have a melting point or glass transition temperature of at least about 60° C., more preferably at least about 90° C., even more preferably at least about 110° C., most preferably at least about 120° C. These other polymers include, for example, the hydrolytically cleavable polyesters as previously described, thermoplastic poly(vinyl alcohol) compositions, cellulose esters, hydroxypropyl cellulose, and starch IPNs.

In preferred embodiments, the particular PHA (or other polymer which may be employed to impart thermomechanical integrity as previously described) is selected primarily according to its melting point. Preferably, the PHA or other polymer has a melting point that is greater than the maximum temperature to which the product will be exposed during any secondary fabrication, storage, or end use. For example, PHBV copolymers with less than about 20 mol % 3-hydroxyvalerate are particularly useful in compositions or products with maximum exposure temperatures of less than 120° C. For compositions to be used in backsheet applications, the PHA (or other polymer imparting thermomechanical integrity as previously described) preferably has a melting point of at least about 60° C., more preferably at least about 90° C., even more preferably at least about 110° C., most preferably at least about 120° C.

It has been surprisingly found that polyhydroxyalkanoates can be used to impart thermomechanical integrity at relatively low levels as compared to other polymers that tend to impart thermomechanical integrity. For example, as little as 10 weight % of the polyhydroxyalkanoate may be needed to impart thermomechanical integrity to the composition. This is important since the use of such low levels tends to minimize the negative influence on mechanical properties and/or melt processing which may occur due to the presence of the polyhydroxyalkanoate. In comparison, other polymers that tend to impart thermomechanical integrity, as previously described, typically must be used at levels in excess of about 30 weight % to achieve the same level of thermomechanical integrity. At these higher levels, limitations associated with such other polymers may significantly reduce the processability and/or other properties of the composition.

The thermomechanical benefits of the polyhydroxyalkanoate are achieved when the composition is processed by melt extrusion methods. Surprisingly, it has been found that these benefits are not realized to the same extent when the same composition is processed by the methods of solution casting or compression molding. Without intending to be limited by theory, it is believed that extrusion processing results in the formation of a substantially continuous network of the polyhydroxyalkanoate within the polymeric product. In other methods, it is believed that the polyhydroxyalkanoate does not form a substantially continuous network, but rather forms discrete regions of the PHA which function as a simple filler. Additionally or alternatively, the polymer molecular orientation which results from melt extrusion methods may impart thermomechanical integrity.

A secondary criteria for selecting a PHA is the molecular weight of the PHA. Where the PHA is a minor component, e.g., present in an amount of less than about 15% of the total polymer composition, the molecular weight must be high enough to impart sufficient thermomechanical integrity to the composition as required for a given application. For most applications, including films and fiber products to be used in disposable absorbent articles, good thermomechanical integrity is typically achieved with a PHA number average molecular weight in the range of from about $10^4$–$10^6$ grams/mole. Number average molecular weights in the range of from about 100,000 to about 900,000 grams/mole are preferred.

The structure of the particular PHA also influences the mechanical properties and the melt processability of the composition. For example, racemic PHB and random copolyesters of 3-hydroxybutyrate with either 3-hydroxyhexanoate, 3-hydroxyoctanoate or 3-dodecanoate can result in films with mechanical properties that are significantly better than either PHB or PHBV. In general, the former PHA polymers tend to provide stronger, more flexible films than the latter polymers. Certain effects are described, for example, in U.S. Pat. No. 5,191,037 issued to Doi et al. on Mar. 2, 1993, incorporated herein by reference. However, the former polymers also tend to have relatively long set times, which in turn tends to make melt processing more difficult. For example, the relatively long crystallization rates of racemic PHB polymers are described in "Miscibility and Morphology of Blends of Isotactic and Atactic Poly(3-hydroxybutyrate)," H. Abe and Y. Doi, *Macromolecules*, 27, pp. 50–54 (1994), incorporated herein by reference. The particular PHA may be selected by the skilled artisan in light of the teachings herein to provide a suitable combination of mechanical properties and melt processing properties.

Polyhydroxyalkanoates are generally employed in an amount of at least about 10% by weight, based on the total weight of the biodegradable polymers in the blend. The thermomechanical integrity of the compositions herein tend to increase with increasing PHA content, with a maximum thermomechanical integrity benefit typically occurring in the range of from about 20 to about 25 weight % PHA. Polymer compositions having PHA levels greater than about 25 weight % are not economically preferred. In addition, polymer compositions having PHA at these higher levels tend to exhibit processing difficulties (increased set time and decreased melt strength). Moreover, the higher levels of PHA can degrade the mechanical properties of end products of the composition, especially where the PHA is PHB or PHBV. For all of these reasons, compositions containing more than about 20 to about 25 weight % PHA may not be preferred. For film applications, a practical upper limit of PHA is about 40 to about 45 weight %. This ensures that the PHA is the dispersed phase and thereby minimizes the negatives associated with the PHA in film applications. For fiber applications a practical upper limit is about 70 to about 80 weight % PHA. For fibers, the remainder is typically of a material that imparts sufficient melt strength, e.g., a mechanically limited polymer.

Preferred mechanically limited polymers are polylactides and cellulose esters. These polymers generally impart good melt processing to the composition, and in sufficient levels may impart high thermomechanical integrity. In addition, these materials are compatible with many polymers, with the exception of certain moisture sensitive materials as previously described. In the latter case, it has been found that the thermally sensitive polycaprolactone and polyurethane polymers can be used to compatibilize the moisture sensitive polymers and the mechanically limited polymers, as described herein.

For improving the melt processability of the composition, generally at least about 10 weight % of the mechanically limited polymer is employed. To take advantage of the thermomechanical integrity these materials can impart to the composition, generally greater than about 30 to about 40 weight % is employed. However, when the level exceeds about 30 weight %, an additional polymer, for example, a biodegradable elastomer or polycaprolactone, or a plasticizer may be desired to offset any increase in product stiffness. This is especially true for film applications. In general, plasticizers are more efficient at reducing the stiffness than an elastomer or polycaprolactone. However, plasticizers usually also reduce the tensile strength whereas the aforementioned polymers typically increase the strength. The skilled artisan will be able to select appropriate levels of such polymers and plasticizers in light of the teachings herein to achieve a desired balance between flexibility and strength. For example, the composition may include from about 20 to about 80 weight percent of the mechanically limited polymer and from about 80 to about 20 weight percent of an elastomer, based on the total weight of the biodegradable polymers present in the composition.

Hydrolytically cleavable polyesters are typically used in compositions containing more rapidly biodegradable polymers selected from moisture sensitive polymers, thermally sensitive polymers, polymers difficult to melt process, and mixtures thereof. Blending with such other polymers tends to enhance the initial breakup and ultimate degradation of the polyester polymers. When used, aromatic/aliphatic polyester copolymers typically make up from about 60 weight percent to about 95 weight percent of the blend, based on the total weight of the biodegradable polymers present in the composition. Oxidized ECO copolymers are useful in the compositions of the present invention to impart heat resistance and moisture resistance, and can be employed in amounts ranging from 1 to 99 weight percent of the total weight of the polymers in the composition. High melting aliphatic polyesters may be used in blends with other biodegradable polymers wherein the high melting aliphatic polyester makes up from about 1 to about 99 weight percent of the total weight of the polymers in the composition.

When used in the compositions of the present invention, a biodegradable elastomer tends to lower the tensile modulus and to increase the ultimate elongation, tear strength, impact strength, and moisture resistance relative to the composition. The elastomer is typically used in an amount of from about 10% to about 80%, preferably from about 20% to about 80%, of the total weight of the polymers in the composition. Surprisingly, it has been found that certain compositions including an aliphatic polyester-based polyurethane, which compositions are described below, exhibit synergistic toughening. The tensile strength of extruded products of these compositions tends to exceed that of the individual components of the composition.

Preferred compositions of the present invention include a polyhydroxyalkanoate and one or more polymers selected from polylactides, aliphatic polyester-based polyurethanes, and polycaprolactone. It has been found that such compositions tend to provide a particularly suitable combination of melt processability, mechanical properties, and thermomechanical integrity. Thus, the compositions tend to exhibit a melt strength and set time that are suitable for melt processing to form products having physical integrity. The resultant products may have mechanical properties that enable their use in several applications, including backsheets and topsheets of disposable absorbent articles. The products have thermomechanical integrity as previously described.

The compositions of the present invention may thus include a polyhydroxyalkanoate and at least one second polymer selected from polylactides, aliphatic polyester-based polyurethanes, and mixtures thereof. In alternative preferred embodiments, the composition includes a polyhydroxyalkanoate and polycaprolactone. According to these latter embodiments, the composition additionally includes at least one additional polymer which tends to enhance the melt processability of the composition. Any of the compositions may contain a plasticizer such as described herein, which tends to improve the mechanical properties of the composition.

In those preferred compositions which include a polyhydroxyalkanoate polymer, certain preferred conditions have been identified. For example, it has been found that at least about 10 weight % of the PHA is required to impart a sufficient level of thermomechanical integrity over the range of temperatures which may be encountered in the fabrication and storage of disposable absorbent articles. In addition, the structure of the particular PHA influences the mechanical properties and the melt processability of the composition, as previously described herein.

In those preferred compositions which include an aliphatic polyester-based polyurethane, it is generally preferred to restrict the level of polyurethane in the composition to less than about 80 weight %, based on the total weight of the polymers in the composition. At higher levels of polyurethane, films formed from the composition tend to be too soft, e.g., the tensile modulus tends to fall below about 10,000 psi. In addition, the composition tends to lack sufficient thermomechanical integrity for use in disposable absorbent articles.

Where a plasticizer is included in the preferred compositions, it has been found that at least about 5 to about 10 weight %, based on the total composition, is typically required to achieve meaningful improvements in mechanical properties. Further improvements in mechanical properties tend to occur as the plasticizer level is increased. However, at plasticizer levels greater than about 20 to about 25 weight %, processing tends to become more difficult (melt strength decreases and set time increases) and the product tends to be greasy to the touch. The plasticizer is preferably used in an amount ranging from about 5 to about 25%, more preferably from about 5 to about 20%, most preferably from about 10 to about 20%, based on the total weight of the composition.

Particular embodiments of the preferred compositions of the present invention, which include a polyhydroxyalkanoate, will now be described.

(a) Compositions Including Polyhydroxyalkanoate and Polylactide

According to one preferred embodiment of the present invention, the composition includes at least one polyhydroxyalkanoate and at least one polylactide. For film applications, it is typically preferred to include a plasticizer in the composition.

It has been found that PLA tends to enhance the melt strength and to reduce blocking of the preferred compositions according to the present invention which include PLA. The mechanical properties of the compositions containing PLA can be modified with a plasticizer, as desired, at relatively low plasticizer levels, without reducing the melt processability of the composition. Thus, the resultant composition tends to have an acceptable melt strength and does not tend to block unacceptably, and may be modified with a plasticizer as may be necessary to obtain desired mechanical properties. Without intending to be limited by theory, it is believed that the melt processing benefits are due in part to the very low level of miscibility of PLA and PHA. Other polymers, e.g., plasticized CAP such as Eastman Chemical Products CAP-H4 series, are highly miscible with PHA both in the melt and in the solid state. It has been found by the present inventors that such miscibility increases the polymer set time and thereby the extent of blocking, such that melt processing is hindered. Moreover, compositions primarily formed from PHA and a cellulose ester tend to require a higher level of plasticizer to achieve a given set of mechanical properties, as compared to compositions primarily formed from PHA and PLA. Thus, the former compositions tend to have a greasy feel.

According to this embodiment of the invention, the composition may contain from about 10% to about 80% polyhydroxyalkanoate and, respectively, from about 90% to about 20% polylactide, based on the total weight of these polymers. These levels of PHA and PLA tend to provide a compatible blend having a desirable combination of thermomechanical integrity and melt processability. Preferably, the composition contains from about 20% to about 60% polyhydroxyalkanoate and, respectively, from about 80% to about 40% polylactide, based on the total weight of these polymers. This composition unexpectedly exhibits synergistic mechanical properties (e.g., the ultimate elongation and tear strength of a blend of these polymers exceeds that of the individual polymers).

The compositions formed from a polyhydroxyalkanoate and a polylactide are particularly suitable for forming fibers and for use in topsheet applications. For film applications, the composition preferably additionally contains a plasticizer as previously described, typically from about 10 to about 20% plasticizer, based on the weight of the composition.

(b) Compositions Including a Polyhydroxyalkanoate and an Aliphatic Polyester-Based Polyurethane In an alternatively preferred embodiment of the present invention, the composition includes at least one polyhydroxyalkanoate and at least one aliphatic, polyester-based polyurethane. For forming films, the composition preferably includes from about 20% to about 80% polyhydroxyalkanoate and, respectively, from about 80% to about 20% polyurethane, based on the total weight of these polymers. This composition tends to provide compatible blends having a suitable combination of thermomechanical integrity, melt processability, and mechanical properties. More preferably, the composition contains from about 20% to about 55% polyhydroxyalkanoate and, respectively, from 80% to about 45% polyurethane, based on the total weight of these polymers. It has surprisingly been found that these compositions exhibit synergistic mechanical properties which are preferred, for example, in backsheets.

For forming fibers and nonwovens, it will typically be preferred to employ levels of PHA of from about 60 to about 90 weight %, based on the total weight of the biodegradable polymers in the composition.

(c) Compositions Including a Polyhydroxyalkanoate, an Aliphatic Polyester-Based Polyurethane, and a Polylactide In another preferred embodiment of the present invention, at least one aliphatic polyester based polyurethane and at least one polylactide are used together in the composition including polyhydroxyalkanoate. This composition preferably contains from about 10% to about 70% polyhydroxyalkanoate, from about 10% to about 70% polylactide, and from 20% to about 80% polyurethane, based on the total weight of these polymers in the composition. These compositions tend to provide compatible or semicompatible blends having a suitable combination of thermomechanical integrity, melt processability, and mechanical properties. In general, the higher the polyurethane content, the better the overall mechanical properties of the products formed from the composition. More preferably, the composition contains from about 10% to about 45% polyhydroxyalkanoate, from about 10% to about 45% polylactide, and from about 45% to about 80% polyurethane, based on the total weight of these polymers in the composition. These compositions tend to provide physical properties which are suitable for use in backsheets. In addition, these compositions provide sufficient thermomechanical integrity to withstand the storage and fabrication processes associated with disposable absorbent articles. For forming films, it may be desired to include a plasticizer in the composition in order to lower the modulus of the film. This will typically be preferred where the film is to be used as a backsheet for disposable absorbent articles. Typically, at least about 5% plasticizer is employed, based on the weight of the composition.

(d) Compositions Including a Polyhydroxyalkanoate, Polycaprolactone. and an Additional Biodegradable Polymer Which Enhances Melt Processability In an alternatively preferred embodiment of the present invention, the composition includes at least one polyhydroxyalkanoate, polycaprolactone, and at least one additional biodegradable polymer which enhances the melt processing of the blend relative to a blend of PHA and PCL. Without intending to be bound by theory, it is believed that the additional polymer modifies the melt rheology of a blend of PHA and PCL. It is believed that this reduces the draw resonance that has been found to occur when melt processing binary blends of a PHA and PCL. In addition, the effective melt strength of the composition is believed to be increased relative to the individual components.

It has been surprisingly found that the additional polymer enhances the melt processability of a variety of different compositions including PHA and PCL. In contrast, typical process enhancers such as antiblocking agents, nucleating agents, and the like are not as universally applicable in these compositions. Indeed, these types of enhancers were found to limit the number of different compositions that could be extrusion processed into products.

Suitable additional polymers for enhancing the melt processability include polylactides; aliphatic polyester-based polyurethanes; thermoplastic poly(vinyl alcohol) compositions; starch-based interpenetrating networks; hydroxypropylcellulose; cellulose esters; and mixtures thereof.

(d)(1) Embodiment wherein the additional polymer is an aliphatic Polyester-based Polyurethane According to one embodiment of the present invention, the composition contains a polyhydroxyalkanoate, polycaprolactone, and at least one aliphatic polyester-based polyurethane. Preferably, the composition contains from about 10% to about 70% PHA, from about 20% to about 80% polycaprolactone, and from about 10% to about 70% polyurethane, based on the total weight of these polymers in the composition. These compositions tend to provide compatible or semicompatible blends having a suitable balance of thermomechanical integrity, melt processability, and mechanical properties. In general, the higher the level of polycaprolactone and polyurethane, the better the overall mechanical properties of products formed from the composition. A particularly preferred composition contains from about 15% to about 55% polyhydroxyalkanoate, from about 35% to about 75% polycaprolactone, and from about 10% to about 50% polyurethane, based on the total weight of these polymers in the composition. These compositions tend to provide films that are particularly suitable for use as a backsheet in disposable absorbent articles. In particular, these compositions provide physical properties suitable for a backsheet and sufficient thermomechanical integrity to withstand both the storage and fabrication processes typically associated with disposable absorbent articles.

(d)(2) Embodiment wherein the additional polymer is a polylactide

In another preferred embodiment of the present invention, the composition contains a polyhydroxyalkanoate, polycaprolactone, and at least one polylactide. These compositions have surprisingly been found to be processable by blown film methods into films having exceptional physical uniformity, without the need for conventional processing aids such as anti-block agents. Preferably, the composition contains from about 10% to about 70% PHA, from about 20% to about 80% polycaprolactone, and from about 10% to about 70% polylactide, based on the total weight of these polymers in the composition. These compositions tend to provide compatible or semicompatible blends having a suitable balance of thermomechanical integrity, melt processability, and mechanical properties. In general, the higher the level of polycaprolactone, the better the overall mechanical properties of products formed from the composition. It has been unexpectedly found that a sharp break in mechanical properties occurs at about equal levels of the polyhydroxyalkanoate and polycaprolactone, with preferred mechanical properties being obtained with a PCL:PHA weight ratio of greater than about 1:1. A particularly preferred composition contains from about 10% to about 45% polyhydroxyalkanoate, from about 45% to about 80% polycaprolactone, and from about 10% to about 45% polylactide, based on the total weight of these polymers in the composition. These compositions provide films that are particularly suitable for use as a backsheet in disposable absorbent articles. In particular, these compositions provide physical properties suitable for a backsheet and sufficient thermomechanical integrity to withstand both the storage and fabrication processes typically associated with disposable absorbent articles.

For forming films, it may be desired to include a plasticizer in the composition in order to lower the modulus of the film. This will typically be preferred where the film is to be used as a backsheet for disposable absorbent articles. Typically, at least about 5% plasticizer is employed, based on the weight of the composition. A plasticizer may be particularly preferred in compositions containing high levels of PHA and/or PLA, e.g., greater than about 25 weight % of the polymers in the composition. For example, it has been found that a plasticizer is preferred where the PHA is PHB or PHBV and the total amount of PHA and PLA is more than about 25 weight % of the polymers in the composition. Compositions containing other PHAs having lower tensile moduli than PHB or PHBV may not require a plasticizer to provide suitable flexibility.

(d)(3) Embodiment wherein the additional polymer is a mixture of a polylactide and an aliphatic polyester-based polyurethane In another preferred embodiment of the present invention, at least one aliphatic polyester-based polyurethane and at least one polylactide are used together in the composition including the polyhydroxyalkanoate and polycaprolactone. Such compositions preferably include from about 10% to about 70% PHA, about 10% to about 70% polycaprolactone, about 10% to about 70% PLA, and about 10% to about 70% polyurethane, based on the total weight of these polymers in the composition. These compositions tend to provide compatible or semicompatible blends having a suitable combination of thermomechanical integrity, melt processability, and mechanical properties. In general, the higher the combined level of polycaprolactone and polyurethane, the better the overall mechanical properties. More preferably, the compositions include from about 10% to about 45% polyhydroxyalkanoate, from about 25% to about 60% polycaprolactone, from about 10% to about 45% PLA, and from about 20% is to about 55% polyurethane, based on the total weight of these polymers in the composition. These compositions provide physical properties suitable for a backsheet and sufficient thermomechanical integrity to withstand both the storage and fabrication processes typically associated with disposable absorbent articles.

For forming films, it may be desired to include a plasticizer in the composition in order to lower the modulus of the film. A plasticizer may be used as previously described for compositions containing polyhydroxyalkanoate, polycaprolactone, and polylactide.

(d)(4) Embodiment wherein the additional polymer is selected from thermoplastic polyvinyl alcohol compositions, starch IPNs, hydroxypropyl cellulose, cellulose esters, and mixtures thereof In yet another preferred embodiment of the present invention, the composition includes polyhydroxyalkanoate, polycaprolactone, and at least one additional polymer selected from thermoplastic polyvinyl alcohol compositions, starch IPNs, hydroxypropyl cellulose, and cellulose esters.

Compositions according to this embodiment of the invention preferably include from about 10% to about 60% PHA, from about 30% to about 80% PCL, and, in combination, from about 10% to about 60% of one or more of the above-mentioned additional polymers, based on the total weight of the biodegradable polymers in the composition. These compositions tend to provide compatible or semicompatible blends having a suitable combination of thermomechanical integrity, mechanical properties, and melt processability. In general, the higher the polycaprolactone level, the better the overall mechanical properties. It has been unexpectedly found that a sharp break in mechanical properties occurs at about equal levels of the polyhydroxyalkanoate and polycaprolactone, with preferred mechanical properties being obtained with a PCL:PHA ratio of greater than about 1:1. More preferably, the compositions contain from about 10% to about 45% polyhydroxyalkanoate, from about 45% to about 80% polycaprolactone, and, in a combined amount, from about from about 10% to about 45% of one or more of the above-mentioned additional polymers, based on the total weight of these polymers in the composition. These compositions provide films that are particularly suitable for use as a backsheet in disposable absorbent articles. In particular, these compositions provide physical properties suitable for a backsheet and sufficient thermomechanical integrity to withstand both the storage and fabrication processes typically associated with disposable absorbent articles.

For forming films, it may be desired to include a plasticizer in the composition in order to lower the modulus of the film. This will typically be preferred where the film is to be used as a backsheet for disposable absorbent articles. Typically, from about 5% to about 15% plasticizer is employed, based on the weight of the composition. A plasticizer is particularly preferred in compositions containing high levels of PHA, hydroxypropylcellulose, and/or cellulose ester, e.g., greater than about 30 weight % of the total polymers in the composition.

It has been found that the preferred amounts of certain additional polymers may vary depending on the identity and relative weight ratios of the polymers. More particularly, where the additional polymer is a thermoplastic polyvinyl alcohol composition, a starch IPN, or a mixture thereof, the preferred total amount of these moisture sensitive polymers generally depends on the relative amounts of the polyhydroxyalkanoate, polycaprolactone, and any polylactide which may be present in the composition. Preferred percentages of the moisture sensitive polymer as a function of the relative weight ratios of PCL to the combined amount of PHA and/or PLA were previously described in a more general reference to compositions containing a PHA and a thermoplastic polyvinyl alcohol composition and/or starch IPN.

(e) Other Compositions Containing a Polymer for Enhancing Melt Processability

Although not required for practicing the present invention, other compositions may also include a polymer for enhancing the melt processability of the composition. For example, the melt processability of a blend of a polyhydroxyalkanoate and a polylactide and/or aliphatic polyester-based polyurethane may be enhanced by incorporating a different, additional polymer from those described above. However, it has been found that in such blends, the utility of the additional polymer may be limited. In particular, where the additional polymer is a thermoplastic polyvinyl alcohol composition, starch IPN, or a mixture thereof, polymer incompatibilities as previously described may arise. Preferred percentages of the moisture sensitive polymer as a function of the relative weight ratios of polyurethane to the combined amount of PHA and/or PLA were previously described in a more general reference to compositions containing a PHA and a thermoplastic polyvinyl alcohol composition and/or starch IPN.

(f) Other Compositions of the Present Invention

The present invention also encompasses compositions derived from other blends of polymers. These compositions tend to provide compatible or semicompatible blends having good thermomechanical integrity, mechanical properties, and/or melt processability. The compositions can include two or more biodegradable polymers to provide binary blends, ternary blends, etc. Such blends may be used to form products, such as films, fibers and nonwovens, which are useful in a variety of applications.

In one alternative embodiment of the present invention, the composition includes at least one moisture sensitive polymer and at least one second polymer selected from hydrolytically cleavable aromatic/aliphatic polyester copolymers, oxidized ethylene/carbon monoxide copolymers, and high melting aliphatic polyesters. The composition typically includes from about 1–40 weight percent, preferably about 1–30 weight percent, of the moisture sensitive polymer(s) and, respectively, from about 99–60 weight percent, preferably about 99–70 weight percent, of the second polymer(s), the weight percentages being based on the total weight of the moisture sensitive polymer(s) and the second polymer(s) in the composition. In a particularly preferred embodiment, the moisture sensitive polymer is selected from thermoplastic polyvinylalcohol compositions, starch IPNs and mixtures thereof.

In another alternative embodiment of the present invention, the composition includes from about 1–60 weight percent of at least one thermally sensitive polymer, and, respectively, from about 99–40 weight percent of at least one second polymer selected from hydrolytically cleavable aromatic/aliphatic polyester copolymers, oxidized ethylene carbon/monoxide copolymers, high melting aliphatic polyesters, and elastomers, the weight percentages being based on the total weight of the thermally sensitive polymer(s) and the second polymer(s) in the composition. In a preferred embodiment, the thermally sensitive polymer is selected from polycaprolactone, aliphatic polyester-based polyurethanes, and mixtures thereof.

Another embodiment of the present invention is a composition containing from about 30–70 weight percent of at least one mechanically limited polymer and from about 70–30 weight percent of at least one elastomer, the weight percentages being based on the total weight of the mechanically limited polymer(s) and the elastomer(s) in the composition. In a preferred embodiment, the mechanically limited polymer is selected from cellulose esters, polylactides, and mixtures thereof; and the elastomer is selected from aliphatic polyester-based polyurethanes.

Additional ternary or higher component blends according to the present invention preferably include at least one thermally sensitive polymer, more preferably polycaprolactone. In alternative embodiments, the thermally sensitive polymer(s) is blended with one or more polymers selected from moisture sensitive polymers, elastomers, mechanically limited polymers, hydrolytically cleavable aromatic/aliphatic polyester copolymers, and oxidized ethylene/carbon monoxide copolymers.

Thus, one alternative composition according to the present invention includes at least one moisture sensitive polymer, at least one thermally sensitive polymer, and at least one elastomer. In a preferred embodiment, the moisture sensitive polymer is selected from thermoplastic polyvinylalcohol compositions, starch IPNs, and mixtures thereof; the thermally sensitive polymer is polycaprolactone; and the elastomer is selected from aliphatic polyester-based polyurethanes.

In another embodiment of the present invention, the composition includes at least one moisture sensitive polymer, at least one thermally sensitive polymer, and at least one mechanically limited polymer. In a preferred embodiment, the moisture sensitive polymer is selected from thermoplastic polyvinylalcohol compositions, starch IPNs, and mixtures thereof; the thermally sensitive polymer is selected from polycaprolactone, aliphatic polyester-based polyurethanes, and mixtures thereof; and the mechanically limited polymer is selected from cellulose esters, polylactides, and mixtures thereof.

In yet another embodiment of the present invention, the composition contains at least one thermally sensitive polymer, at least one mechanically limited polymer, and at least one elastomer. In a preferred embodiment, the thermally sensitive polymer is polycaprolactone; the mechanically limited polymer is selected from cellulose esters, polylactides, and mixtures thereof; and the elastomer is selected from aliphatic polyester-based polyurethanes.

Another embodiment of the invention is a composition including at least one hydrolytically cleavable aromatic/aliphatic polyester copolymer, at least one thermally sensitive polymer, and at least one moisture sensitive polymer. In a preferred embodiment, the thermally sensitive polymer is selected from polycaprolactone, aliphatic polyester-based polyurethanes, and mixtures thereof; and the moisture sensitive polymer is selected from thermoplastic polyvinylalcohol compositions, starch IPNs, and mixtures thereof.

A composition of the present invention may also be formed from a blend of at least one oxidized ethylene/carbon monoxide copolymer, at least one thermally sensitive polymer, and at least one moisture sensitive polymer. In a preferred embodiment, the thermally sensitive polymer is selected from polycaprolactone, aliphatic polyester-based polyurethanes, and mixtures thereof; and the moisture sensitive polymer is selected from thermoplastic polyvinylalcohol compositions, starch IPNs, and mixtures thereof.

OPTIONAL COMPONENTS

In addition to the above-mentioned components, the compositions of the present invention may contain other components as may be, or later become, known in the art, including, but not limited to, plasticizers, antiblocking agents, antistatic agents, slip agents, pro-heat stabilizers, antioxidants, pro-oxidant additives, pigments, etc. Antiblocking agents, antistatic agents and slip agents are typically employed in compositions to be used for forming films. Pro-heat stabilizers, antioxidants and pro-oxidant additives are typically employed in compositions to be melt processed.

Plasticizers may be used in the composition to modify the mechanical properties of products formed from the composition. In general, plasticizer tends to lower the modulus and tensile strength, and to increase the ultimate elongation, impact strength, and tear strength of the polymeric product. The plasticizer may also be used to lower the melting point of the composition to thereby enable melt processing at lower temperatures and to minimize energy requirements and thermal degradation. The use of a plasticizer may therefore be particularly useful in compositions containing high melting polymers, e.g., certain polyhydroxyalkanoates. For example, a plasticizer may be particularly useful for this purpose with compositions containing PHB and PHBV with less than about 12 mol % hydroxyvalerate.

Several plasticizing compounds are known in the art and are suitable for use herein. Suitable plasticizers are exemplified by glycerol triacetate, methyl ricinolate, dihexyl phthalate, low molecular weight polycaprolactone diol or polycaprolactone triol (typically having number average molecular weights of less than about 1000 grams per mole), acetyltri-n-butyl citrate, and others such as those described in the above referenced U.S. Pat. No. Nos. 3,182,036 and 5,231,148.

Antiblocking agents act to prevent film layers from sticking to one another when wound into a roll or when disposable articles are packaged in contact with one another. Typical antiblocking substances include concentrates of silica or talc blended with a polymeric material such as polyethylene or polycaprolactone. Reduction of blocking in the films of the present invention can also be obtained by loading the film surface with small particles or powders such as chalk, clay, silica, starch, and similar materials. Powdered polymeric materials (e.g., polytetrafluoroethylene) can also be used to reduce blocking when applied to the surface of films of the present invention. Such film surface treatments can be used to reduce blocking alone or in combination with other antiblock methods. The quantity of powder antiblock substance commonly added to the surface of a film, when used, is from about 0.5 g/m$^2$ to about 5 g/m$^2$.

Antistatic agents may be incorporated in films of the present invention; examples of such agents include ethoxylated amines and quaternary amine salts having organic constituents of about 12–18 carbon atoms in length. Agents of this type slowly defuse to the surface of the film and, because of their ionic character, form an electrically conductive layer on the surface of the film. Antistatic agents commonly constitute from about 1% to about 5% of the weight of the films, when used.

Slip agents may be incorporated into the films of the present invention to reduce drag over rollers and other forming equipment. Examples of such agents are those commonly derived from amides of fatty acids having about 12 to 22 carbon atoms. Such agents may augment the antiblocking properties of the films of the present invention. Such slip agents are commonly incorporated in films from about 0.05% to about 3% of the weight of the films when used.

APPLICATIONS

The compositions of the present invention can be melt processed into several forms, including films, fibers, nonwovens, bottles and other containers, and other shaped articles.

The polymeric compositions herein can be processed into fibers by methods such as are known in the art, for example, melt spinning and melt blowing. Processes for forming nonwovens from fibrous materials are also well known. For example, the nonwoven may be spunbonded, melt blown, air-laid, carded, hydroentangled, combinations of the forementioned, and the like. The nonwoven may be thermally bonded by means well known to those skilled in the fabrics art.

The compositions of the present invention are also suitable for forming films such as are known in the art, including continuous films, apertured films, including hydroformed films and vacuum formed films, and the like. The films may be processed using conventional procedures for producing films of blended polymers on conventional film making equipment. The compositions herein are particularly well-suited for processing by melt extrusion methods. Liquid impervious films for use as a backsheet material are typically either cast or blown films.

In general, melt extrusion methods involve blending of the above-described polymeric components followed by extrusion of the blend. Pellets of the polymeric components can be first dry blended and then melt mixed in the film extruder itself. Alternatively, if insufficient mixing occurs in the film extruder, the pellets can be first dry blended and then melt mixed in a pre-compounding extruder followed by repelletization prior to film extrusion.

Melt extrusion methods suitable for forming films of the present invention include cast or blown film extrusion methods, both of which are described in *Plastics Extrusion Technology*, 2nd Ed., Allan A. Griff (Van Nostrand Reinhold-1976), herein incorporated by reference. In a cast film method, the molten blend is extruded through a linear slot die. Generally the resultant flat web is cooled on a large moving polished metal roll. It quickly cools, and peels off this first roll, passes over one or more auxiliary cooling rolls, then through a set of rubber-coated pull or "haul-off" rolls, and finally to a winder. A method of making a cast backsheet film for the absorbent products of the present invention is described below in the Examples.

In blown film extrusion (also referred to as tubular film extrusion), the molten blend is extruded upward through a thin annular die opening to form a tube. Air is introduced through the center of the die to inflate the tube and causes it to expand. A moving bubble is thus formed which is held at constant size by control of internal air pressure. The tube of film is cooled by air blown through one or more chill rings surrounding the tube. The tube is next collapsed by drawing it into a flattening frame through a pair of pull rolls and into a winder. For backsheet applications the flattened tubular film is subsequently slit open, unfolded, and further slit into widths appropriate for use in absorbent articles.

Both cast film and blown film processes can be used to produce either monolayer or multilayer film structures. For the production of monolayer films from a single thermoplastic material or blend of thermoplastic components only a single extruder and single manifold die are required.

PERFORMANCE CRITERIA AND TEST METHODS

As previously stated, the films formed from the compositions of the present invention may be particularly well-suited for use as a biodegradable, liquid impervious backsheet in disposable absorbent articles such as diapers and feminine products. The backsheets of disposable articles should have sufficient strength both to process on a high speed disposable article converting machine and to provide a "wetproof" barrier when the article is in use. It must be sufficiently wetproof so that clothing or bedding, either that of the wearer and/or of the caregiver, is not wet or soiled. It preferably has a modulus or flexibility that is, at the same time, low enough to be a soft, pleasing material to be used as the outer covering of the article, yet high enough to handle easily on high speed disposable article converters without wrinkling, folding, or creasing. It must have sufficient resistance to heat such that it will not deform, melt, or permanently lose strength in typical hot storage conditions or, as applicable, lose its integrity on high speed disposable article converting lines, which typically use heat tunnels or hot melt adhesives to bond the components of a disposable article together.

For a film to perform satisfactorily as a biodegradable backsheet, it must be made of resins or structures that are biodegradable and it must demonstrate, at room temperature, the following properties of high tear and impact strength, adequate fluid barrier as measured by moisture transport rate, and appropriate tensile modulus. Suitable backsheets also preferably have an appropriate elongation at break and tensile strength. Where the backsheet material will be exposed to temperatures above room temperature during conversion, storage, or use, it must also have sufficient thermomechanical integrity to withstand such exposure without significant negative impact on its physical integrity or mechanical properties. Since absorbent articles may experience temperatures as high as 140° F. (60° C.) during warehouse storage or shipping in trucks or railcars, or even as high as 195° F. (90° C.) or more during converting operations where the films are used to fabricate absorbent articles, it is important that the backsheet film retain its integrity at these temperatures. Although it is expected that the modulus of the films will decrease somewhat as the temperature increases from room temperature to such elevated temperatures, the modulus should not decrease too far as to allow the film to rip during conversion or to deform in the package before it reaches the end user.

It has been found that films that are sufficiently strong to be suitable as biodegradable backsheets for disposable articles demonstrate two properties: (a) resistance to tearing (tear propagation resistance or tear strength) in both the machine direction and the cross-machine direction of manufacture, and (b) resistance to rupture from a dropped weight (i.e., impact strength).

In general, the tear strengths should be as high as possible consistent with the realization of other properties preferred for a backsheet. Preferably, the backsheet demonstrates, at room temperature, an average tear strength of at least about 25 grams, more preferably at least 50 grams, still more preferably at least about 70 grams, per 25.4 micron thickness of material in both the machine direction and the cross-machine direction. Most preferred are those backsheets that demonstrate, at room temperature, tear strengths of 100 or more grams per 25.4 micron thickness in the cross-machine direction because these are particularly good at avoiding a tendency to fail in use by splitting. Tear strength can be determined using a testing machine such as the Instron Model 1122 following ASTM D 1938-85. As used herein, the tear strength is the average tear strength calculated from five separate measurements. As will be understood by the skilled artisan, the samples are selected and mounted in the testing machine so as to measure the tear strength in the desired direction of manufacture.

Impact strength can be determined by a falling ball drop method such as are known in the art. Preferred biodegradable backsheets of the present invention can withstand the drop of a spherical steel ball of about 19 millimeters in diameter and 27.6 to 28.6 gram mass from a height of 12 centimeters so that at least 50% of the tests result in no rupture of any size (deformation is acceptable). Preferred materials are those that exhibit 50% or less failures (i.e., does not rupture) from a height of more than 20 centimeters.

Films of sufficient barrier to moisture for use in diapers are those that permit less than 0.001 grams of synthetic urine to pass into an absorbent paper towel per square centimeter of area per 25.4 micron thickness for every 16 hours of time when the test film is located between the absorbent paper towel and a typical absorbent gelling material-containing diaper core and a pressure simulating that of a baby. The specific conditions of the test are that the area of the core is larger than that of the test material, the core is loaded with synthetic urine to its theoretical capacity and it is under a weight of about 35 g/cm$^2$ (0.5 psi).

It has been found that materials of sufficient modulus for use as backsheets demonstrate a tensile (Young's) modulus in the machine direction of manufacture of at least about 6.895×10$^8$ dynes/cm$^2$ and below about 6.895×10$^9$ dynes/cm$^2$ at room temperature. In addition, preferred films for use as a backsheet have a tensile strength in the machine direction of manufacture of at least about 20 MPa and an elongation at break (i.e., ultimate elongation) in the machine direction of manufacture of greater than about 140%, both at room temperature. The tensile modulus, strength, and ultimate elongation can be determined using a testing machine such as the Instron Model 1122 following ASTM D 882-3. The values stated herein are the average of at least five separate measurements. As will be understood by the skilled artisan, the samples are selected and elongated on the tensile testing machine so as to measure the tensile properties in the machine direction of manufacture.

Thermomechanical integrity can be quantified by the Vicat softening temperature, melting point, and/or by the dynamic storage modulus in tension as a function of temperature of the polymeric product.

The backsheets must not melt or exhibit thermoplastic flow to an extent which renders them unsuitable for their intended use, under conditions of storage, conversion, and use. In addition, preferred backsheets demonstrate a Vicat softening point of at least 45° C. Vicat softening is tested using a Heat Distortion Apparatus Model No. CS-107 or equivalent and a modification of ASTM D-1525. The modification is in the preparation of the sample. According to the present invention, a 19 square millimeter size film of 4.5 to 6.5 micron thickness is prepared for Vicat needle penetration tests by melting the material to be tested into a mold of using a temperature of 120° C. and a pressure of 7.031×10$^5$ g/cm$^2$ (10,000 psi) (using a Carver or similar press) for two minutes after a warmup period of at least 2 minutes. The Vicat softening point is the temperature at which a flat-ended needle of 1 mm$^2$ circular cross section will penetrate the sample to a depth of 0.1 cm under a load of 1000 g using a uniform temperature rise rate of 50° C. per hour.

Preferred backsheet materials have a dynamic storage modulus in tension, E', in the machine direction of manufacture of at least 20 MPa at temperatures above about 60° C., more preferably above about 90° C., even more preferably above about 110° C., most preferably above about 120° C. Stated another way, the preferred backsheets are defined by having a specified failure temperature, which is the temperature at which the modulus falls below 20 MPa as previously described. Preferred backsheets have a failure temperature of at least about 60° C., more preferably at least about 90° C., even more preferably at least about 110° C., most preferably at least about 120° C.

The dynamic storage modulus and its dependence on temperature, also called a modulus/temperature spectrum, of the films herein can be measured on a dynamic mechanical analyzer (DMA) such as the Autovibron instrument available from Imass, Inc. of Norwell, Mass. Many other types of DMA devices exist, and the use of dynamic mechanical analysis to study the modulus/temperature spectra of polymers is well known to those skilled in the art of polymer characterization. This information is well summarized in two books: *Dynamic Mechanical Analysis of Polymeric Material, Materials Science Monographs Volume 1*, T. Murayama (Elsevier Publishing Co. 1978); and *Mechanical Properties of Polymers and Composites, Volume 1*, L. E. Nielsen (Marcel Dekker 1974), both incorporated herein by reference.

The mechanism of operation and procedures for using the Autovibron are found in the Imass user instruction manual entitled "Automation System for Rheovibron Viscoelastometer," revised July, 1982, incorporated herein by reference. To those skilled in the use of the Autovibron or equivalent instruments, the following run conditions will be sufficient to replicate the sample failure temperature data presented hereinafter.

To measure the modulus/temperature spectrum of a film specimen, the Autovibron,is run in a temperature scan mode and equipped with an extension measuring system (EMS). A film specimen approximately 3 mm wide, 0.0254 mm thick, and of sufficient length to allow 4 to 5 cm of length between the specimen grips is mounted in the grips. The sample is selected and mounted such that the DSM is determined in the machine direction of manufacture. The apparatus is then enclosed in an environmental chamber swept with nitrogen gas. Stress is applied to the film in the length direction to achieve a deformation or strain of about 0.1 percent of the original length. A dynamic sinusoidal strain is applied to the specimen at a frequency of 110 cycles per second. The temperature is increased at a rate of 1° C. per minute from room temperature to the point where the specimen melts or breaks. Temperature-dependent behavior is characterized by monitoring changes in strain and the phase difference in time between stress and strain. Storage modulus values in mega-Pascals (1 MPa; $1.0 \times 10^6$ dynes/cm$^2$) are calculated by the computer along with other data and displayed as functions of temperature on a video display terminal. The data are saved on computer disk and a hard copy of the storage modulus/temperature spectrum is printed for further review. The failure temperature, i.e., the temperature at which the storage modulus drops below 20 MPa, is determined directly from the spectrum.

Preferred compositions for use in fiber applications and in nonwoven, including topsheet, applications, have the following properties as determined on a 12–75 micron thick film: (a) a tensile modulus in the machine direction of manufacture of at least about 1000 MPa; and (b) a tensile strength in the machine direction of manufacture of at least about 20 MPa. These tensile properties can be determined as described above. Compositions that provide films having these tensile properties tend to provide acceptable fibers and nonwoven products. In addition, preferred compositions for use in fiber applications to be used in disposable absorbent articles provide films having a dynamic storage modulus in the machine direction of manufacture of at least 20 MPa at temperatures above about 60° C., more preferably above about 90° C., even more preferably above about 110° C., most preferably above about 120° C. Stated another way, preferred compositions for use in such fiber applications provide films that are defined by a specified failure temperature, which is the temperature at which the modulus in the machine direction of manufacture falls below 20 MPa as previously described. Preferred compositions for use in such fiber applications provide films having a failure temperature of at least about 60° C., more preferably at least about 90° C., even more preferably at least about 110° C., most preferably at least about 120° C. The DSM and failure temperature can be determined as described above. Compositions that provide films having this DSM or failure temperature tend to provide fibers and nonwoven products having a thermomechanical integrity that is preferred for disposable absorbent article applications.

DISPOSABLE ABSORBENT ARTICLES

As previously stated, the compositions of the present invention are useful in components of disposable absorbent articles. As used herein, the term "absorbent article" refers to devices which absorb and contain body exudates, and more specifically, refers to devices which are placed against the skin of a wearer to absorb and contain the various exudates discharged from the body. The term "disposable" is used herein to describe absorbent articles which are not intended to be laundered or otherwise restored or reused as an absorbent article after a single use. Examples of disposable absorbent articles to which the present invention can be adapted include feminine hygiene garments such as sanitary napkins and panti-liners, diapers, incontinence briefs, diaper holders, training pants, and the like.

Disposable absorbent articles typically have a liquid pervious topsheet, a liquid impervious backsheet joined to the topsheet and an absorbent core positioned between the topsheet and the backsheet. Disposable absorbent articles and components thereof, including the topsheet, backsheet, absorbent core, and any individual layers of these components, have a body surface and a garment surface. As used herein, "body surface" means that surface of the article or component which is intended to be worn toward or adjacent to the body of the wearer, while the "garment surface" is on the opposite side and is intended to be worn toward or placed adjacent to the wearer's undergarments, or away from the wearer's body, when the disposable absorbent article is worn. As positioned in the absorbent article while worn, the topsheet is typically adjacent the body, while the backsheet is typically positioned away from the wearer's body.

In a preferred embodiment, the topsheet and/or the backsheet of the disposable absorbent article includes a polymer composition of the present invention. Although the polymer composition can be incorporated in any suitable form, it is preferably incorporated in the form of a film as the backsheet, and/or in the form of a nonwoven web or an apertured film as the topsheet. Alternatively, the backsheet and topsheet may independently include topsheet or backsheet materials such as are now known or as become known in the art. For example, the topsheet or backsheet may be formed of materials described in any of the patents or patent applications referenced below in regard to diapers and sanitary napkins.

Films formed from the compositions of the present invention are especially well suited for use as the backsheet. Film materials used as liquid impervious backsheets in absorbent articles will typically have a thickness of from 0.01 mm to about 0.2 mm, preferably from 0.012 mm to about 0.051 mm.

The topsheet should be compliant, soft-feeling, and non-irritating to the wearer's skin. Further, the topsheet is liquid pervious, permitting liquids to readily penetrate through its thickness. As an alternative to the polymeric compositions of the present invention, a suitable topsheet may be manufactured from a wide range of materials such as porous foams, reticulated foams, apertured plastic films, natural fibers (e.g., wood or cotton fibers), other synthetic fibers (e.g., polyester or polypropylene fibers) or from a combination of natural and synthetic fibers. Preferably, the topsheet is made of a hydrophobic material to isolate the wearer's skin from liquids in the absorbent core. Where a conventional topsheet material is used, a particularly preferred topsheet for use in diapers comprises staplelength polypropylene fibers having a denier of about 1.5, such as Hercules type 151 polypropylene marketed by Hercules, Inc. of Wilmington, Del. As used herein, the term "staple-length fibers" refers to those fibers having a length of at least about 16 mm.

There are a number of manufacturing techniques which may be used to manufacture a nonwoven topsheet. For example, the topsheet may be woven, non-woven, spunbonded, carded, or the like. For use in diapers, a preferred topsheet is carded, and thermally bonded by means well known to those skilled in the fabrics art. Preferably, the diaper topsheet has a basis weight from about 18 to about 25 g/m$^2$, a minimum dry tensile strength of at least about 400 g/cm in the machine direction, and a wet tensile strength of at least about 55 g/cm in the cross-machine direction.

The topsheet and the backsheet are joined together in any suitable manner. As used herein, the term "joined" encompasses configurations whereby the topsheet is directly joined to the backsheet by affixing the topsheet directly to the backsheet, and configurations whereby the topsheet is indirectly joined to the backsheet by affixing the topsheet to intermediate members which in turn are affixed to the backsheet. In a preferred embodiment, the topsheet and the backsheet are affixed directly to each other in the periphery of the disposable absorbent article by attachment means such as an adhesive or any other attachment means as known in the art. For example, a uniform, continuous layer of adhesive, a patterned layer of adhesive, or an array of separate lines or spots of adhesive may be used to affix the topsheet to the backsheet.

The absorbent core of the diaper is positioned between the topsheet and backsheet. The absorbent core may be manufactured in a wide variety of sizes and shapes (e.g., rectangular, hour-glass, asymmetrical, etc.) and from a wide variety of materials. The total absorbent capacity of the absorbent core should, however, be compatible with the designed liquid loading for the intended use of the absorbent article. Further, the size and absorbent capacity of the absorbent core may vary to accommodate wearers ranging from infants through adults. A preferred embodiment of the diapers of the present invention has a hour-glass shaped absorbent core. The absorbent core is preferably an absorbent member containing a web or batt of airfelt (wood pulp fibers), and a particulate absorbent polymeric composition disposed therein.

In addition to a topsheet, backsheet, and absorbent core, the disposable absorbent articles of the present invention may further include other components as are known in the art. For example, diapers can include a fastening system and elastic members such as elastic leg members. Fastening systems, elastic members, and other suitable components of diapers and sanitary napkins are described in the patents or patent applications referenced below in regard to diaper and sanitary napkin configurations.

Diapers are one type of absorbent article of the present invention. While the topsheet, the backsheet, the absorbent core and other members may be assembled in a variety of well known configurations, a preferred diaper configuration is described generally in U.S. Pat. No. 3,860,003, entitled "Contractible Side Portion for Disposable Diaper" which issued to Kenneth B. Buell on Jan. 14, 1975, and which patent is incorporated herein by reference. Additional diaper configurations that are preferred for use herein are disclosed in U.S. Pat. No. 5,151,092 issued to Buell et al. on Sep. 29, 1992; U.S. Pat. No. 5,221,274 issued to Buell et al. on Jun. 22, 1993; and in co-pending U.S. patent application Ser. No. 08/203,456; filed on Feb. 28, 1994. Each of these patents and the application are incorporated herein by reference.

Other examples of absorbent articles according to the present invention are sanitary napkins designed to receive and contain vaginal discharges such as menses. Disposable sanitary napkins are designed to be held adjacent to the human body through the agency of a garment, such as an undergarment or a panty or by a specially designed belt. Examples of the kinds of sanitary napkins to which the present invention is readily adapted are shown in U.S. Pat. No. 4,687,478, entitled "Shaped Sanitary Napkin With Flaps" which issued to Kees J. Van Tilburg on Aug. 18, 1987; U.S. Pat. No. 4,589,876, entitled "Sanitary Napkin" which issued to Kees J. Van Tilburg on May 20, 1986; U.S. Pat. No. 4,950,264, "Thin, Flexible Sanitary Napkin" issued to Osborn on Aug. 21, 1990; U.S. Pat. No. 4,425,130, "Compound Sanitary Napkin" issued to DesMarais on Jan. 10, 1984; U.S. Pat. No. 4,321,924, "Bordered Disposable Absorbent Article" issued to Ahr on Mar. 30, 1982; U.S. Pat. No. 5,009,653 "Thin, Flexible Sanitary Napkin" issued to Osborn on Apr. 23, 1991, and U.S. Pat. No. 5,308,346 "Elasticized Sanitary Napkin" issued to Sneller, et al. on May 3, 1994. Each of these patents are incorporated herein by reference. It will be apparent that films formed of the polymeric compositions described herein may be used as the liquid impervious backsheet of such sanitary napkins. On the other hand it will be understood the present invention is not limited to any specific sanitary napkin configuration or structure.

Importantly, the absorbent articles according to the present invention are compostable to a greater extent than conventional absorbent articles which employ certain conventional materials, for example, a polyolefin backsheet.

"Compostability," "compostable," and the like means the ability of a material to undergo physical, chemical, thermal, and/or biological degradation in a municipal solid waste (hereinafter "MSW") composting facility such that the material will break down into, or otherwise become part of, usable finished compost. To be considered compostable, a material must also ultimately fully biodegrade in the environment in a manner similar to paper and yard waste.

Municipal solid waste (MSW) composting processes generally involve three sequential phases: waste preparation, active composting, and curing. During the waste preparation phase, raw MSW is first sorted to remove recyclables and known non-compostable materials. The sorted materials are then reduced in physical size, generally via a grinder or rotating drum such as are known in the composting art. The goal is to obtain a consistent physical size, typically particles of about 2" diameter, which will maximize surface area for microbial attack and allow effective air management during the subsequent active composting phase. Following size reduction, materials are usually screened through a 1.5"–2" screen. In order to be compostable by this process, a material must be capable of being reduced in size such that it passes through this screen. The rejected (>1.5"–2") fraction is typically landfilled.

Although size reduction via grinder is largely independent of the relative chemical or biological degradability of a material, the rotating drum technology offers opportunities for engineered material characteristics that promote size reduction. The rotating drum process is microbiologically active with a duration of several days, typically 3 days. During the process, free moisture is available (at least about 35% w/w, typically 50% w/w), an acidic environment develops (pH 4.5–5.5), and the temperature increases (typically to from about 40° C. to about 50° C.). Hydrolytically unstable materials often degrade in this environment such that their physical integrity is compromised and they pass the 1.5"–2" barrier.

In the active composting phase, the size-reduced materials from the waste preparation phase are arranged into self-insulating configurations, such as piles or trenches. The mass is kept moist (at least about 35% w/w moisture, typically about 50% w/w moisture), is periodically mixed to distribute nutrients and expose new surfaces for microbial attack, and is force-aerated to supply oxygen and to control temperature. The waste serves as physical support as well as a source of organic and inorganic nutrients for indigenous microbes. The major form of metabolism is aerobic respiration. One of the metabolic by-products, heat, tends to be retained within the matrix, causing self-heating. Temperatures commonly reach 65° C. or higher. At the beginning of active composting, the pH is typically acidic but can increase to as high as 8.5 by the completion of this portion of the process. Further degradation, both chemical and biological, takes place during this phase and typically results in further size reduction. After several weeks of active composting (typically 5–7 weeks), the mass is screened through the final size barrier, a ⅜"–½" screen. In order to be compostable by this process, the material must be capable of being made to pass through this screen. Rejects (>⅜"–½") from this separation step are typically landfilled.

The final phase, curing, requires the least intervention. Although many complex organic materials, including biodegradable synthetic polymers, continue to degrade after curing, this phase marks the final step of the managed composting process prior to utilization. In this phase, static piles of the actively composted material sit undisturbed for a period of several weeks to a few months. During this phase, mesophilic microorganisms as well as microfauna colonize the compost. As organic substrate availability decreases, microbial activity decreases and selfheating subsides. In order to be compostable by this process, the material must form an integral part of the usable finished compost and ultimately completely biodegrade in the environment in a manner and at a rate consistent with materials such as paper and yard waste.

The relative rates at which polymeric products are biodegraded can be assessed using a modified Sturm test or by an Organic Waste System (i.e., OWS) method. The modified Sturm test is a dilute, aqueous, aerated test. The OWS method is a controlled composting biodegradation test. Both tests are based on the fact that during the aerobic biodegradation of organic materials, carbon dioxide is the primary carbon-containing decomposition product which is generated. The cumulative $CO_2$ production can be determined by monitoring and integrating the evolved $CO_2$ in the exhaust stream from a test reactor. The percentage biodegradation can then be calculated as the percentage of carbon in the test material (determined by standard physico-chemical methods) which is converted to $CO_2$. The Sturm test employs an inoculum derived from the supernatant of a settled, activated sludge from a waste water treatment facility. The inoculum in the OWS test consists of a mature, stabilized fraction of municipal solid waste. Details of these techniques are found in "Ready Biodegradation: Modified Sturm Test;" OECD Method #301B; and in "Standard Test Method for Determining Aerobic Biodegradation of Plastic Materials under Controlled Composting Conditions," ASTM Method #D5338-92; each test method being incorporated herein by reference.

Products formed from the polymeric compositions of the present invention tend to have a more rapid rate of biodegradation than conventional backsheet materials such as polyethylene. In addition, in the initial MSW phase, the products of the present invention tend to be more readily fragmented than such conventional materials. Thus, absorbent articles containing polymeric products of these polymeric compositions tend to be more readily biodegraded and composted than such articles containing such conventional materials.

EXAMPLES

The following examples illustrate the practice of the present invention but are not intended to be limiting thereof.

Cast and blown film blends as noted are prepared by the following general procedure. For each blend composition, a total of about 1500 grams is first dry blended in a Kelly Duplex mixer for 15 minutes. The dry blend is then melt compounded in a Haake Rheomix TW-100 twin screw extruder with conical barrels and two partially intermeshing counterrotating venting screws and equipped with a single-strand horizontal rod die and a 0.125 inch (0.3175 cm) diameter nozzle. The temperature profile of the extruder varies from 275° F. (135° C.) in the first heating zone, to 310° F. (154° C.) in the second zone, and 340° F. (171° C.) in the third zone at the discharge end near the die, while the die temperature is held constant at 250° F. (121° C.). The screw speed is maintained at 25 rpm. The molten strand is cooled and solidified in a water bath prior to entering a Berlyn Model PEL-2 pelletizer where it is chopped into pellets approximately 0.125 inches (0.3175 cm) long. The cooled pellets are then dried in a vacuum oven at 122° F. (50° C.) for four hours prior to film processing.

Where the composition includes one or more plasticizers, a Zenith metering pump Series BPB, available from Parker Hannifin Corp., is used to inject the plasticizer into the extruder at the first zone melt thermocouple port. The motor speed of the pump is adjusted so as to obtain the approximate desired level of plasticizer. The actual plasticizer level is determined by measuring the resulting melting and/or glass transition temperature by dynamic mechanical analysis as described above and comparing these temperatures to a calibration curve of melt/glass transition temperature versus plasticizer level. The calibration curve is constructed by solution blending the polymers with known amounts of plasticizer and then determining the resultant melt/glass transition temperatures by DMA. This method of determining component percent composition via DMA is well known in the art.

Cast film is produced from the compounded pellets using a Haake Rheomix Model 202 0.75 inch (1.905 cm) diameter single screw extruder equipped with a 6 inch (15.24 cm) wide horizontal sheet die utilizing a 0.04 inch (0.1016 cm) die gap. A constant taper screw having a 20:1 length to diameter ratio and a 3:1 compression ratio is employed. The temperature of the first heating zone is maintained at 320° F. (160° C.), the second heating zone at 355° F. (179° C.), and the die at 275° F. (135° C.). Screw speed is maintained at 20 rpm. The molten film passes from the die to a Postex sheet take-off system where it is cooled and collected on a cardboard core. Take-off speed is adjusted to provide a film about 4.5 inches (11.4 cm) wide and 0.002 inches (50.8 microns) thick.

Blown film is produced from the compounded pellets using the Haake Rheommix TW-100 twin-screw extruder described above equipped with a 1 inch spider die and a 6 inch air cooling ring. The temperature profile of the extruder varies from 315° F. (157° C.) in the first heating zone, to 355° F. (179° C.) in the second zone, and 375° F. (191° C.) in the third zone at the discharge end near the die, while the die temperature is held constant at 310° F. (154° C.). The screw speed is maintained at 15 rpm. The molten tube passes from the die and is inflated by blowing air into the tube through an air duct inside the die. The inflated tube is cooled by chilled air from the air cooling ring, and then collapsed by a set of nip rolls at the top of the blown film take-off tower. The collapsed tube is then collected on a cardboard core. The blow-up ratio (ratio of the bubble is diameter to the die exit diameter) and the vertical take-off speed are adjusted to provide a film tube about 2–4 inches (5.08–10.16 cm) in diameter and 0.002 inches (54.8 microns) thick.

Unless otherwise noted, the films of the following examples are cast films.

The abbreviations in the following examples represent these materials:

CAP-H4 cellulose acetate propionate having 7 weight % plasticizer, available from Eastman Kodak CAP-MH cellulose acetate propionate having 17 weight % plasticizer, available from Eastman Kodak CAP-S2 cellulose acetate propionate having 31 weight % plasticizer, available from Eastman Kodak PCL polycaprolactone, Union Carbide TONE P-787

PHBV poly(3-hydroxybutyrate-co-3-hydroxyvalerate), with either 5.5, 8.1, 12, or 22.3 mol % 3-hydroxyvalerate (HV), available from Zeneca Bioproducts PLA polylactic acid, available from Cargill, Inc.

Pu1 aliphatic polyester-based polyurethane, Morton International PN3429-100

PU2 aliphatic polyester-based polyurethane, Morton International PN03-204

Vinex 2034, 2019 plasticized polyvinyl alcohol, Air Products

Mater-Bi starch based interpenetrating network composition, Novamont AF05H

CA4 Citroflex A4, an acetyltri-n-butyl citrate plasticizer from Morflex, Inc.

GTA triacetin, a plasticizer, from Aldrich Chemical Co.

In addition, the examples identified with a prefix of "CE" in the following Tables represent Comparative Examples outside the scope of the invention.

(I) PCL/other degradable polymer (binary blend) Films formed from a blend of a polycaprolactone polymer and other degradable polymers, and their respective properties, are shown in Table I.

The above examples show that various degradable polymers combined with polycaprolactone provide certain mechanical properties and thermomechanical integrity which are preferred for backsheet materials which must withstand elevated temperatures that may be encountered during absorbent article storage or converting processes. The polyurethane at the noted levels did not impart a degree of thermomechanical integrity which is preferred for use in backsheets.

PHBV imparts a degree of thermomechanical integrity which is most preferred for backsheets, while maintaining tensile and tear properties that are more preferred for backsheet materials. These blends provide products that can withstand elevated temperatures that may be encountered during absorbent article storage or converting processes. However, the PHBV/PCL blends exhibit draw resonance. Such draw resonance can be sufficiently reduced by the addition of about 10% or greater of a third degradable polymer which acts as a process enhancer. Suitable examples of such compositions are given below.

As shown, higher levels of CAP-H4 (greater than about 40 weight %) provide the thermomechanical integrity necessary for a film to withstand the elevated temperatures that may be encountered in absorbent article conversion processes. However, at these levels, the extension at break is relatively low such that these PCL/CAP-H4 blends tend not to provide each of the mechanical properties that are preferred for backsheet materials. In addition, the set time for the polycaprolactone/cellulose ester blends tends to be too long for conventional film (cast and blown), fiber and nonwoven cycle times.

The examples also show that polylactide can provide a level of thermomechanical integrity that is preferred for backsheet materials, but does not provide a level of thermomechanical integrity that to withstand the typical elevated temperatures that may be encountered in absorbent article conversion processes. If the composition contains greater than about 20 weight % isotactic PLA and if the polymeric product is sufficiently annealed after manufacture, the PLA component becomes fully crystallized and can then impart sufficient thermomechanical integrity to withstand such conversion processes. Since such post-shaping steps are generally impractical and tend to destroy the molecular orientation which is important for end use mechanical properties, such steps are not preferred.

For PLA levels greater than about 40 weight %, the tensile modulus of the film becomes too high for backsheet applications. A plasticizer may be added as described herein to provide tensile moduli suitable for backsheet applications.

The examples show that the blends containing greater than about 20 weight % of the moisture sensitive polymers Vinex and Mater-Bi can provide a level of thermomechanical integrity that is preferred for backsheets. Higher levels of the moisture sensitive polymer (greater than about 30 weight %) are required to provide the thermomechanical integrity sufficient to withstand the typical elevated temperatures that may be encountered during an absorbent article conversion process. However, at these levels, the blend is very moisture sensitive. Thus, the moisture transport rate tends to be greater than the values preferred for backsheet applications.

(II) PHA/PCL/PU Films formed from several compositions containing polyhydroxyalkanoate, polycaprolactone, and polyurethane are prepared as shown in Table II.

The PU component eliminates the draw resonance associated with the PHA/PCL blend. There is a high level of compatibility between these materials as evidenced by the synergistic behavior in the tensile strength for a given ratio of PHA to PCL. For many of these blends, relatively low levels of the PHA component are required to maintain a failure temperature which is preferred for backsheet materials which must withstand typical elevated temperatures that may be encountered during converting processes. As the ratio of PHA to PCL increases, the range of PU concentrations that results in compositions which provide the mechanical properties preferred for backsheets decreases.

Blend numbers 1–5, 8, 10–13, 16, 22 and 23 represent compositions that are most preferred for backsheet films which must withstand conversion processes at typical elevated temperatures. The incorporation of about 5–15% plasticizer into Blend number 9 would reduce the film tensile modulus to a level which is preferred for backsheet materials. Blend numbers 17 and 18 are compositions which are preferred for fiber and nonwoven topsheet applications that must withstand elevated temperatures that may be encountered during absorbent article converting processes.

(III) PHA/PCL/PLA Films formed from several blends of polyhydroxyalkanoate, polycaprolactone, and polylactide are prepared, as shown in Table III.

The PLA component eliminates the draw resonance associated with the PHA/PCL blend. In addition, the PLA is a good process enhancer for blown film. For many of these blends, relatively low levels of the PHA component are required to provide a failure temperature which is preferred for backsheet materials which must withstand the elevated temperatures that are typical of absorbent article conversion processes. The addition of plasticizer increases the flexibility and toughness of the films.

Blend numbers 4 and 7 represent compositions that provide mechanical properties that are preferred for backsheet films, and which provide sufficient thermomechanical integrity to withstand the elevated temperatures that may be encountered in disposable absorbent article conversion processes. The incorporation of about 5–15% plasticizer would reduce the tensile modulus of blend numbers 3 (which is equivalent to number 11), 5, 6 (equivalent to 13), and 8 (equivalent to 14) to levels preferred for backsheet materials. Blend numbers 6 and 8, which are equivalent to 13 and 14, respectively, represent compositions that are preferred for fiber and nonwoven topsheet applications which must withstand the elevated temperatures that are typical of absorbent article conversion processes.

(IV) PHA/PCL+third polymer (PVOH or Starch IPN) Films formed from several blends of polyhydroxyalkanoate, polycaprolactone, and either a thermoplastic polyvinyl alcohol composition (PVOH, Vinex) or a starch IPN composition (Mater-Bi), as shown in Table IV.

The Vinex or the Mater-Bi component eliminates the draw resonance associated with the PHA/PCL blend. When the level of PHA exceeds the level of PCL in the blend, the incompatibility between the PHA and either Vinex or the Mater-Bi results in a significant drop in mechanical property performance (see blend numbers 7–9).

Blend numbers 1–6 represent compositions that are preferred for backsheet films which must withstand the typical elevated temperatures that may be encountered during absorbent article conversion processes; while blend number 7 represents a composition suitable for fiber and nonwoven topsheet applications which must withstand the elevated temperatures that may be encountered during absorbent article conversion processes.

(V) PHA/PU Films formed from several blends of polyhydroxyalkanoate and polyurethane are prepared, as shown in Table V.

These blends show a high level of compatibility between the PHA and PU components as evidenced by the synergistic behavior in the tensile strength. The PHA component can impart sufficient thermomechanical integrity to withstand the elevated temperatures that are typically encountered during absorbent article converting processes, even at relatively low levels of 10%. The compositions containing PU1 provide mechanical properties which are preferred for backsheet materials. In addition, the PU improves the overall melt processability by imparting good melt strength.

Blend numbers 3–5 represent compositions which provide mechanical properties that are suitable for backsheet films; while blend number 9 represents a composition which provides mechanical properties that are suitable for fiber or nonwoven topsheet applications.

(VI) PHA/PLA Several blends of polyhydroxyalkanoate and polylactide are prepared as shown in Table VI.

These blends show a high level of compatibility, as evidenced by the synergistic behavior in the extension at break and the tear strength relative to the individual polymers. The blends provide levels of thermomechanical integrity which are preferred for backsheet materials that must withstand the elevated temperatures that are typical of absorbent article converting processes, even with relatively low levels of PHBV. The addition of plasticizer increases the flexibility and toughness of the films.

Blend numbers 2–5 and 7, especially numbers 2 and 3, represent compositions that provide mechanical properties that are preferred for fiber and nonwoven topsheet applications. Due to the low tear strength of these blends, they are not preferred for use as a backsheet material.

(VII) PHA/PLA/PU Films formed from several blends of polyhydroxyalkanoate, polylactide, and polyurethane are prepared as shown in Table VII. The addition of PU improves the flexibility and toughness of the PHA/PLA films of Table VI.

The blends provide sufficient thermomechanical integrity to withstand the elevated temperatures that may be encountered during absorbent article converting processes. Blend numbers 2, 5, 6–8 and 10 represent compositions having mechanical properties that are suitable for fiber and nonwoven topsheet applications. The incorporation of about 5–15% plasticizer into Blend numbers 2, 3, and 5 would reduce the film tensile modulus to a level which is preferred for backsheet materials.

(VIII) PCL/PLA/PVOH Several blends of polycaprolactone, polylactide, and a thermoplastic polyvinyl alcohol composition are prepared as shown in Table VIII. The PVOH is Vinex 2019 from Air Products.

The blends containing both PLA and PVOH provide sufficient thermal integrity to withstand the elevated temperatures that may be encountered during absorbent article converting processes.

Blend number 5 represents a composition that provides the mechanical properties that are preferred for backsheet films. If a blown film were prepared from Blend number 4 rather than the cast film shown in Table VII, it is expected that the blown film would have the mechanical properties that are preferred for backsheet films.

(IX) CAP/PU Films formed from several blends of cellulose acetate propionate and aliphatic polyester-based polyurethane are prepared as shown in Table IX.

There is a high level of compatibility between the CAP and PU as evidenced by the synergistic behavior in the tensile strength for each of the three grades of CAP relative to the individual polymers. The compositions that include at least 40 weight % CAP provide sufficient thermomechanical integrity to withstand the elevated temperatures that may be encountered during absorbent article converting processes. In comparison, PHBV provided similar thermomechanical integrity levels at levels of only 10 weight % (see Table V). As the CAP plasticizer level increases, the films become softer (lower modulus) and extend further for a given ratio of CAP-to-PU. However, the tensile and tear strength generally decrease.

Blend numbers 5, 11, and 16 represent compositions that provide mechanical properties that are preferred for backsheet films. Blend numbers 2, 3 and 8 represent compositions that provide mechanical properties that are preferred for fiber and nonwoven topsheet applications.

(X) PCL+two from CAP-H4, PVOH or PU Several blends of polycaprolactone and cellulose acetate propionate, thermoplastic polyvinyl alcohol composition, or polyurethane are prepared as shown in Table X.

Blend 2 may be suitable for use as a backsheet material where the thermomechanical integrity of the material is not critical, e.g., where the material will not be exposed to temperatures above about room temperature. Blend numbers 1 and 3 do not possess each of the mechanical properties that are preferred for backsheet materials.

TABLE I

| Blend number | wt % PCL | wt % other degradable polymer | Caliper (mil) | Modulus (MPa) | Tensile strength (MPa) | Ultimate elongation (%) | Tear strength (MD/CD) (g/mil) | E' at 60° C. (MPa) | Failure Temperature (° C.) |
|---|---|---|---|---|---|---|---|---|---|
| CE 1 | 100 | 0 | 2.0 | 229 | 49 | 1200 | 195/250 | 3 | 58 |
| 2 | 90 | 10% PHBV (5.5% HV) | 2.7 | 438 | 37 | 875 | 143/— | 73 | 127 |
| 3 | 80 | 20% PHBV (5.5% HV) | 2.0 | 621 | 30 | 729 | 159/242 | 123 | 157 |
| 4 | 80 | 20% CAP-H4 | 2.0 | 299 | 37 | 845 | 286/308 | 6 | 57 |
| 5 | 60 | 40% CAP-H4 | 2.0 | 578 | 29 | 94 | 156/108 | 27 | 147 |
| 6 | 80 | 20% PLA | 2.0 | 685 | 34 | 658 | 151/144 | 182 | 65 |

TABLE I-continued

| Blend number | wt % PCL | wt % other degradable polymer | Caliper (mil) | Modulus (MPa) | Tensile strength (MPa) | Ultimate elongation (%) | Tear strength (MD/CD) (g/mil) | E' at 60° C. (MPa) | Failure Temperature (° C.) |
|---|---|---|---|---|---|---|---|---|---|
| 7  | 60 | 40% PLA        | 2.0 | 888 | 20 | 243 | 59/48   | 487 | 68  |
| 8  | 80 | 20% PU1        | 2.0 | 191 | 43 | 470 | 118/116 | 6   | 55  |
| 9  | 60 | 40% PU1        | 2.0 | 141 | 53 | 359 | 71/102  | 6   | 51  |
| 10 | 80 | 20% Vinex 2034 | 2.0 | 374 | 35 | 750 | 238/276 | 48  | 61  |
| 11 | 60 | 40% Vinex 2034 | 1.8 | —   | —  | —   | —       | 200 | 167 |
| 12 | 80 | 20% Mater-Bi   | 2.0 | 278 | 32 | 641 | —       | 33  | 83  |

TABLE II

| Blend number | wt % PHBV (5.5% HV) | wt % PCL | wt % PU | PHBV:PCL | Caliper (mil) | Modulus (MPa) | Tensile strength (MPa) | Ultimate elongation (%) | Tear strength (MD/CD) (g/mil) | Failure Temperature (° C.) |
|---|---|---|---|---|---|---|---|---|---|---|
| 1    | 20 | 80  | 0   | 20:80 | 2.0 | 621  | 30 | 729 | 159/242 | 157 |
| 2    | 18 | 72  | 10  | 20:80 | 3.0 | 579  | 38 | 602 | 124/215 | 157 |
| 3    | 16 | 64  | 20  | 20:80 | 2.0 | 470  | 36 | 407 | 65/128  | 162 |
| 4    | 12 | 48  | 40  | 20:80 | 2.0 | 314  | 56 | 395 | 46/107  | 154 |
| 5    | 8  | 32  | 60  | 20:80 | 2.0 | 233  | 53 | 347 | 47/134  | 153 |
| 6    | 4  | 16  | 80  | 20:80 | 2.0 | 71   | 57 | 343 | 33/101  | 63  |
| CE 7 | 0  | 0   | 100 | —     | 2.0 | 3    | 23 | 503 | 120/138 | 37  |
| 8    | 30 | 50  | 20  | 37:63 | 2.0 | 684  | 27 | 519 | 99/199  | 152 |
| 9    | 40 | 60  | 0   | 40:60 | 2.5 | 896  | 28 | 750 | 126/176 | 163 |
| 10   | 38 | 57  | 5   | 40:60 | 2.0 | 680  | 24 | 571 | 104/153 | 164 |
| 11   | 36 | 54  | 10  | 40:60 | 2.0 | 636  | 28 | 558 | 84/164  | 162 |
| 12   | 32 | 48  | 20  | 40:60 | 2.0 | 600  | 32 | 409 | 68/118  | 162 |
| 13   | 24 | 36  | 40  | 40:60 | 2.0 | 484  | 40 | 352 | 37/104  | 163 |
| 14   | 16 | 24  | 60  | 40:60 | 2.0 | 331  | 69 | 238 | 14/139  | 160 |
| 15   | 8  | 12  | 80  | 40:60 | 2.5 | 71   | 66 | 223 | 10/100  | 57  |
| 16   | 30 | 40  | 30  | 43:57 | 2.0 | 656  | 33 | 468 | 55/147  | 152 |
| 17   | 80 | 20  | 0   | 80:20 | 7.0 | 1292 | 20 | 5   | 18/45   | 163 |
| 18   | 76 | 19  | 5   | 80:20 | 3.0 | 1074 | 20 | 8   | 9/—     | 163 |
| 19   | 72 | 18  | 10  | 80:20 | 2.0 | 960  | 21 | 407 | 6/—     | 163 |
| 20   | 64 | 16  | 20  | 80:20 | 2.0 | 783  | 20 | 340 | 7/—     | 162 |
| 21   | 48 | 12  | 40  | 80:20 | 2.0 | 757  | 39 | 332 | 11/73   | 160 |
| 22   | 32 | 8   | 60  | 80:20 | 2.0 | 591  | 66 | 286 | 32/153  | 164 |
| 23   | 16 | 4   | 80  | 80:20 | 2.2 | 224  | 67 | 294 | 27/114  | 163 |

TABLE III

I) Cast Film

| Blend number | wt % PHBV | wt % PCL | wt % PLA | wt % plasticizer | PHBV:PCL | Caliper (mil) | Modulus (MPa) | Tensile strength (MPa) | Ultimate elongation (%) | Tear strength (MD/CD) (g/mil) | Failure Temperature (° C.) |
|---|---|---|---|---|---|---|---|---|---|---|---|
| 1 | 0           | 80 | 20 | 0                     | —     | 2.0 | 685  | 34 | 658 | 151/144 | 70  |
| 2 | 0           | 60 | 40 | 0                     | —     | 2.0 | 888  | 20 | 243 | 59/48   | 70  |
| 3 | 16 (5.5% HV)| 64 | 20 | 0                     | 20:80 | 2.0 | 878  | 32 | 489 | 111/171 | 157 |
| 4 | 14 (5.5% HV)| 56 | 20 | 10 (6% CA-4; 4% GTA)  | 20:80 | 2.0 | 365  | 28 | 667 | 82/178  | 150 |
| 5 | 14 (5.5% HV)| 56 | 30 | 0                     | 20:80 | 1.0 | 970  | 32 | 300 | 51/107  | 158 |
| 6 | 32 (8.1% HV)| 48 | 20 | 0                     | 40:60 | 2.0 | 1139 | 25 | 454 | 68/95   | 157 |
| 7 | 27 (8.1% HV)| 40 | 20 | 13 (13% CA-4; 7% GTA) | 40:60 | 2.0 | 345  | 21 | 699 | 32/139  | 155 |
| 8 | 28 (8.1% HV)| 42 | 30 | 0                     | 40:60 | 2.0 | 1301 | 25 | 279 | 40/63   | 157 |
| 9 | 48 (8.1% HV)| 32 | 20 | 0                     | 60:40 | 2.0 | 1366 | 18 | 13  | 17/49   | 154 |

TABLE III-continued

II) Blown Film

| Blend number | wt % PHBV (8.1% HV) | wt % PCL | wt % PLA | wt % plasticizer | PHBV:PCL | Caliper (mil) | Modulus (MPa) | Tensile strength (MPa) | Ultimate elongation (%) | Tear strength (MD/CD) (g/mil) | Failure Temperature (° C.) |
|---|---|---|---|---|---|---|---|---|---|---|---|
| 10 | 0 | 80 | 20 | 0 | — | 1.0 | 464 | 26 | 526 | 174/118 | 70 |
| 11 | 16 | 64 | 20 | 0 | 20:80 | 2.5 | 896 | 27 | 401 | 54/— | 147 |
| 12 | 15 | 60 | 20 | 5 (CA-4) | 20:80 | 2.5 | 760 | 26 | 538 | 84/— | 145 |
| 13 | 32 | 48 | 20 | 0 | 40:60 | 2.0 | 1048 | 24 | 337 | 25/96 | 150 |
| 14 | 28 | 42 | 30 | 0 | 40:60 | 2.0 | 1321 | 28 | 137 | 50/87 | 147 |

TABLE IV

| Blend number | wt % PHBV | wt % PCL | PHBV:PCL | wt % third polymer | Caliper (mil) | Modulus (MPa) | Tensile strength (MPa) | Ultimate elongation (%) | Tear strength (MD/CD) (g/mil) | Failure Temperature (° C.) |
|---|---|---|---|---|---|---|---|---|---|---|
| 1 | 20 (5.5% HV) | 80 | 20:80 | 0 | 2.0 | 621 | 30 | 729 | 159/242 | 157 |
| 2 | 19 (5.5% HV) | 76 | 20:80 | 5% Vinex 2034 | 2.5 | 418 | 25 | 764 | 177/410 | 157 |
| 3 | 18 (5.5% HV) | 72 | 20:80 | 10% Vinex 2034 | 2.1 | 480 | 22 | 684 | 122/— | 155 |
| 4 | 17 (5.5% HV) | 68 | 20:80 | 15% Vinex 2034 | 2.0 | 413 | 20 | 651 | 107/324 | 156 |
| 5 | 16 (5.5% HV) | 64 | 20:80 | 20% Vinex 2034 | 2.5 | 500 | 19 | 606 | 46/201 | 157 |
| 6 | 16 (22.3% HV) | 64 | 20:80 | 20% Mater-Bi | 1.7 | 274 | 19 | 583 | 99/224 | 117 |
| 7 | 60 (5.6% HV) | 40 | 60:40 | 0 | 3.5 | 1073 | 17 | 232 | 55/91 | 158 |
| 8 | 54 (5.5% HV) | 36 | 60:40 | 10% Vinex 2019 | 1.8 | 970 | 16 | 215 | 19/88 | 153 |
| 9 | 48 (5.5% HV) | 32 | 60:40 | 20% Vinex 2019 | 2.7 | 688 | 7 | 5 | 7/12 | 152 |

TABLE V

| Blend number | wt % PHBV (5.5% HV) | wt % PU1 | Caliper (mil) | Modulus (MPa) | Tensile strength (MPa) | Ultimate elongation (%) | Tear strength (MD/CD) (g/mil) | Failure Temperature (° C.) |
|---|---|---|---|---|---|---|---|---|
| CE 1 | 0 | 100 | 2.0 | 3 | 23 | 503 | 120/138 | 37 |
| 2 | 10 | 90 | 2.0 | 49 | 65 | 312 | 16/58 | 142 |
| 3 | 20 | 80 | 1.8 | 151 | 62 | 383 | 71/59 | 165 |
| 4 | 30 | 70 | 3.0 | 395 | 52 | 416 | 49/79 | 157 |
| 5 | 40 | 60 | 2.6 | 466 | 47 | 340 | 31/87 | 162 |
| 6 | 50 | 50 | 3.0 | 669 | 45 | 373 | 18/88 | 155 |
| 7 | 70 | 30 | 2.5 | 942 | 28 | 318 | 7/36 | 154 |
| 8 | 80 | 20 | 2.8 | 1180 | 15 | 10 | 7/14 | 163 |
| 9 | 90 | 10 | 2.0 | 1347 | 19 | 2 | 5/9 | 163 |
| CE 10 | 100 | 0 | 2.0 | 1774 | 27 | 3 | 13/18 | 160 |

TABLE VI

| Blend number | wt % PHBV (8.1% HV) | wt % PLA | wt % plasticizer (CA-4) | PHBV:PLA | Caliper (mil) | Modulus (MPa) | Tensile strength (MPa) | Ultimate elongation (%) | Tear strength (MD/CD) (g/mil) | Failure Temperature (° C.) |
|---|---|---|---|---|---|---|---|---|---|---|
| CE 1 | 0 | 100 | 0 | 0:100 | 2.0 | 2350 | 46 | 4 | 6/8 | 73 |
| 2 | 20 | 80 | 0 | 20:80 | 2.0 | 2057 | 37 | 11 | 9/14 | 160 |
| 3 | 40 | 60 | 0 | 40:60 | 2.0 | 1909 | 30 | 15 | 9/15 | 160 |
| 4 | 60 | 40 | 0 | 60:40 | 2.0 | 1842 | 38 | 4 | 8/15 | 157 |
| 5 | 80 | 20 | 0 | 80:20 | 2.0 | 1541 | 32 | 4 | 6/14 | 157 |
| CE 6 | 100 | 0 | 0 | 100:0 | 1.5 | 1439 | 24 | 3 | 7/9 | 160 |
| 7 | 36 | 54 | 10 | 40:60 | 2.0 | 1301 | 19 | 50 | 18/19 | 150 |
| 8 | 34 | 51 | 15 | 40:60 | 2.0 | 642 | 21 | 289 | 12/37 | 150 |

TABLE VII

| Blend number | wt % PHBV (8.1% HV) | wt % PLA | wt % PU | PHBV:PLA | Caliper (mil) | Modulus (MPa) | Tensile strength (MPa) | Ultimate elongation (%) | Tear strength (MD/CD) (g/mil) | Failure Temperature (° C.) |
|---|---|---|---|---|---|---|---|---|---|---|
| 1 | 40 | 60 | 0 | 40:60 | 2.0 | 1909 | 30 | 15 | 9/15 | 160 |
| 2 | 24 | 36 | 40 (PU2) | 40:60 | 2.0 | 1390 | 31 | 413 | 18/36 | 158 |
| 3 | 16 | 24 | 60 (PU2) | 40:60 | 2.0 | 973 | 36 | 492 | 34/78 | 154 |
| CE 4 | 0 | 0 | 100 (PU2) | — | 2.0 | 15 | 43 | 527 | 51/55 | 44 |
| 5 | 12 | 48 | 40 (PU2) | 20:80 | 2.0 | 1371 | 30 | 423 | 15/49 | 156 |
| 6 | 42 | 18 | 40 (PU2) | 70:30 | 2.0 | 1242 | 35 | 527 | 10/41 | 151 |
| 7 | 50 | 20 | 30 (PU2) | 71:29 | 2.0 | 1128 | 30 | 355 | 4/36 | 153 |
| 8 | 50 | 30 | 20 (PU2) | 62.5:37.5 | 2.0 | 1333 | 37 | 405 | 5/29 | 152 |
| 9 | 50 | 20 | 30 (PU1) | 71:29 | 2.0 | 972 | 20 | 250 | 6/20 | 152 |
| 10 | 50 | 30 | 20 (PU1) | 62.5:37.5 | 2.0 | 1334 | 24 | 101 | 4/18 | 153 |

TABLE VIII

| Blend number | wt % PCL | wt % PLA | wt % PVOH (Vinex 2019) | Caliper (mil) | Modulus (MPa) | Tensile strength (MPa) | Ultimate elongation (%) | Tear strength (MD/CD) (g/mil) | Failure Temperature (° C.) |
|---|---|---|---|---|---|---|---|---|---|
| 1 | 80 | 20 | 0 | 2.0 | 685 | 34 | 658 | 151/144 | 65 |
| 2 | 60 | 40 | 0 | 2.0 | 888 | 20 | 243 | 59/48 | 68 |
| 3 | 80 | 0 | 20 | 2.0 | 308 | 23 | 725 | 171/221 | 57 |
| 4 | 70 | 10 | 20 | 2.2 | 396 | 21 | 632 | 23/216 | 120 |
| 5 | 70 | 20 | 10 | 2.0 | 614 | 29 | 638 | 113/175 | 117 |
| 6 | 60 | 20 | 20 | 2.09 | 646 | 29 | 697 | 15/164 | 124 |

TABLE IX

| Blend number | wt % CAP | wt % PU1 | wt % CAP plasticizer level | Caliper (mil) | Modulus (MPa) | Tensile strength (MPa) | Ultimate elongation (%) | Tear strength (MD/CD) (g/mil) | Failure Temperature (° C.) |
|---|---|---|---|---|---|---|---|---|---|
| CE 1 | 100 (CAP-H4) | 0 | 7 | 2.0 | 1523 | 44 | 19 | 9/15 | 176 |
| 2 | 75 (CAP-H4) | 25 | 7 | 2.0 | 1403 | 57 | 30 | 4/9 | 181 |
| 3 | 60 (CAP-H4) | 40 | 7 | 2.0 | 1053 | 65 | 53 | 6/20 | 178 |
| 4 | 50 (CAP-H4) | 50 | 7 | 2.0 | 688 | 64 | 94 | 16/51 | 176 |
| 5 | 40 (CAP-H4) | 60 | 7 | 2.0 | 372 | 56 | 152 | 27/109 | 172 |
| 6 | 25 (CAP-H4) | 75 | 7 | 2.0 | 118 | 63 | 338 | 90/108 | 78 |
| CE 7 | 0 | 100 | 7 | 2.0 | 3 | 23 | 503 | 120/138 | 37 |
| CE 8 | 100 (CAP-MH) | 0 | 17 | 2.0 | 1067 | 33 | 36 | 3/5 | 172 |
| 9 | 80 (CAP-MH) | 20 | 17 | 2.0 | 972 | 32 | 52 | 8/7 | 178 |
| 10 | 60 (CAP-MH) | 40 | 17 | 2.0 | 636 | 41 | 75 | 12/15 | 173 |
| 11 | 40 (CAP-MH) | 60 | 17 | 2.0 | 249 | 43 | 188 | 64/— | 172 |
| 12 | 20 (CAP-MH) | 80 | 17 | 2.0 | 74 | 52 | 354 | 46/91 | 63 |
| CE 13 | 100 (CAP-S2) | 0 | 31 | 2.0 | 573 | 15 | 39 | 4/4 | 107 |
| 14 | 80 (CAP-S2) | 20 | 31 | 2.0 | 409 | 4.5 | 38 | 5/6 | 128 |
| 15 | 60 (CAP-S2) | 40 | 31 | 2.0 | 188 | 10 | 76 | 12/16 | 174 |
| 16 | 40 (CAP-S2) | 60 | 31 | 2.0 | 71 | 50 | 216 | 58/191 | 170 |
| 17 | 20 (CAP-S2) | 80 | 31 | 2.0 | 21 | 58 | 293 | 31/94 | 67 |

TABLE X

| Blend number | wt % PCL | wt % PU | wt % CAP-H4 | wt % PVOH | Caliper (mil) | Modulus (MPa) | Tensile strength (MPa) | Ultimate elongation (%) | Tear strength (MD/CD) (g/mil) | Failure Temperature (°C.) |
|---|---|---|---|---|---|---|---|---|---|---|
| 1 | 50 | 0 | 25 | 25 | 2.0 | 315 | 25 | 255 | 8/22 | 122 |
| 2 | 50 | 25 | 25 | 0 | 2.0 | 171 | 43 | 593 | 182/245 | 58 |
| 3 | 50 | 25 | 0 | 25 | 2.0 | 304 | 38 | 490 | 21/51 | 94 |

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

What is claimed is:

1. A biodegradable, polymer composition, said composition being suitable for melt processing into various forms, including films, fibers, and nonwovens and comprising a compatible or semicompatible polymer blend, said blend consisting essentially of:
   (a) a first, biodegradable polymer, said polymer being a polyhydroxyalkanoate which is selected from the group consisting of homopoly (3-hydroxyalkanoates), homopoly (4-hydroxyalkanoates), copolymers of (3-hydroxyalkanoates) with (4-hydroxyalkanoates), and mixtures thereof,
   (b) at least one polylactide and at least one aliphatic polyester-based polyurethane, and
   (c) the composition comprises from about 10% to about 70% of said polyhydroxyalkanoate, from about 10% to about 70% of said polylactide, and from about 20% to about 80 of said polyurethane, based on the total weight of said polyhydroxyalkanoate, said polylactide, and said polyurethane and from 0 to about 25% of a plasticizer, by weight of the composition.

2. The composition of claim 1 comprising from about 20% to about 60% of said polyhydroxyalkanoate and, respectively, from about 80% to about 40% of said polylactide, based on the total weight of said polyhydroxyalkanoate, said polylactide, and said polyurethane.

3. The composition of claim 1 comprising from about 20% to about 55% of said polyhydroxyalkanoate and, respectively, from about 80% to about 45% of said polyurethane, based on the total weight of said polyhydroxyalkanoate, said polylactide, and said polyurethane.

4. The composition of claim 1 comprising from about 10% to about 45% of said polyhydroxyalkanoate, from about 10% to about 45% of said polylactide, and from about 45% to about 80% of said polyurethane, based on the total weight of said polyhydroxyalkanoate, said polylactide, and said polyurethane.

5. A biodegradable, polymer composition, said composition being suitable for melt processing into various forms, including films, fibers, and nonwovens and comprising a compatible semicompatible polymer blend, said blend consisting essentially of:
   (a) a first biodegradable polymer, said polymer being a polyhydroxyalkanoate which is selected from the group consisting of homopoly (3-hydroxyalkanoates), homopoly (4-hydroxyalkanoate), copolymers of (3-b hydroxyalkanoates with (4-hydroxyalkanoates), and mixtures thereof;
   (b) at least one second, biodegradable polymer, said second polymer being selected from polylactides;
   (c) polycaprolactone; and
   (d) from 0 to about 25% of a plasticizer, by weight of the composition;
   wherein the composition comprises from about 10% to about 70% of said polyhydroxyalkanoate, from about 20% to about 80% of said polycaprolactone, and from about 10% to about 70% of said polylactide, based on the total weight of said polyhydroxyalkanoate, said polycaprolactone, and said polylactide.

6. The composition of claim 5 comprising from about 10% to about 45% of said polyhydroxyalkanoate, from about 45% to about 80% of said polycaprolactone, and from about 10% to about 45% of said polylactide, based on the total weight of said polyhydroxyalkanoate, said polycaprolactone, and said polylactide.

7. A biodegradable, polymer composition, said composition being suitable for melt processing into various forms, including films, fibers, and nonwovens and comprising a compatible or semicompatible polymer blend, said blend consisting essentially of:
   (a) a first, biodegradable polymer, said polymer being a polyhydroxyalkanoate which is selected from the group consisting of homopoly (3-hydroxyalkanoates), homopoly (4-hydroxyalkanoates), copolymers of (3-hydroxyalkanoates) with (4-hydroxyalkanoates, and mixtures thereof;
   (b) at least one second, biodegradable polymer, said second polymer comprising a mixture of at least one aliphatic polyester-based polyurethane and at least one polylactide;
   (c) polycaprolactone; and
   (d) from 0 to about 25% of a plasticizer, by weight of the composition;
   wherein said composition comprises from about 10% to about 70% of said polyhydroxyalkanoate, from about 10% to about 70% of said polycaprolactone, from about 10% to about 70% of said polyurethane, and from about 10% to about 70% of said polylactide, based on the total weight of said polyhydroxyalkanoate, said polycaprolactone, said polyurethane, and said polylactide.

8. The composition of claim 7 comprising from about 10% to about 45% of said polyhydroxyalkanoate, from about 25% to about 60% of said polycaprolactone, from about 20% to about 55% of said polyurethane, and from about 10% to about 45% of said polylactide, based on the total weight of said polyhydroxyalkanoate, said polycaprolactone, said polyurethane, and said polylactide.

* * * * *

UNITED STATES PATENT AND TRADEMARK OFFICE
CERTIFICATE OF CORRECTION

PATENT NO. : 5,939,467
DATED : August 17, 1999
INVENTOR(S) : Wnuk et al.

It is certified that error appears in the above-identified patent and that said Letters Patent is hereby corrected as shown below:

Column 13,
Line 32, after "by" please delete "is".

Column 14,
Lines 1-10, please delete the chemical structure and replace it with:

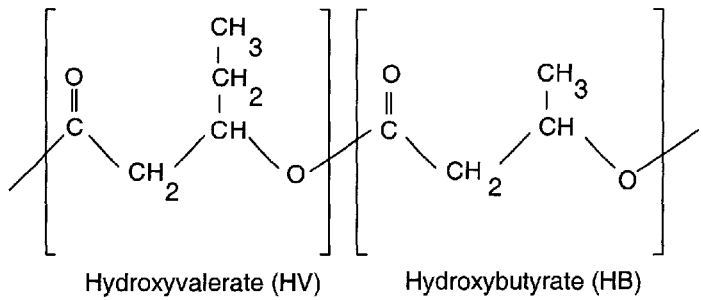

Hydroxyvalerate (HV)    Hydroxybutyrate (HB)

Column 19,
Line 35, please delete "PN03-04" and insert therefor -- PN03-204 --.

Column 29,
Line 29, please delete "is".

Column 38,
Line 37, please delete "staplelength" and insert therefor -- staple-length -- (hyphenated word).

Column 41,
Line 5, please delete "selfheating" and insert therefor -- self-heating --.

Column 42,
Line 45, please delete "is".
Line 64, please delete "Pu1" and insert therefor -- PU1 --.

Column 43,
Line 5, please delete "CA4" and insert therefor -- CA-4 -- (hyphenated).
Line 5, please delete "A4" and insert therefor -- A-4 -- (hyphenated).

UNITED STATES PATENT AND TRADEMARK OFFICE
CERTIFICATE OF CORRECTION

PATENT NO. : 5,939,467
DATED : August 17, 1999
INVENTOR(S) : Wnuk et al.

It is certified that error appears in the above-identified patent and that said Letters Patent is hereby corrected as shown below:

Column 44,
Line 59, please delete "polvmer" and insert therefore -- polymer --.

Column 49,
Table IV, under the second column (wt. % PHBV), Blend number 7, delete "5.6%" and insert therefor -- 5.5% --.

Columns 51-52,
The spacing for the heading for Table VIII is off. Please correct so that "PCL" is under the first "wt %"; "PLA" is under the second "wt %"; "2019)" is under "(Vinex"; "(mil)" is under "Caplier"; "(MPa)" is under "Modulus" and "Tensile strength"; "(%)" is under "Ultimate elongation"; "(g/mil)" is under "(MD/CD)"; and "(º C.)" is under "Temperature".

Table VIII, under 5$^{th}$ column (Caliper (MPa)), delete "2.09" (in Blend number 6) and insert therefore -- 2.0 --.

Column 53,
Line 30, delete "," and insert therefor -- ; -- (semi-colon).
Line 32, delete "," and insert therefor -- ; -- (semi-colon).
Line 36, after "80" insert therefor -- % --.
Line 61, (4$^{th}$ line of Claim 5), between "compatible" and "semicompatible" insert therefor -- or --.
Line 63, (1$^{st}$ line of (a) of Claim 5), after "first" insert therefor -- , -- (a comma).
Line 66, (4$^{th}$ line of (a) of Claim 5), delete "(4-hydroxyalkanoate)" and insert therefore -- (4-hydroxyalkanoates) --. Also in the same line, after "(3-"delete "b".

UNITED STATES PATENT AND TRADEMARK OFFICE
CERTIFICATE OF CORRECTION

PATENT NO.   : 5,939,467
DATED        : August 17, 1999
INVENTOR(S)  : Wunk et al.

It is certified that error appears in the above-identified patent and that said Letters Patent is hereby corrected as shown below:

Column 54,
Line 41, after "(4-hydroxyalkanoates" insert therefor -- ) -- (right parenthesis).

Signed and Sealed this

Nineteenth Day of November, 2002

Attest:

Attesting Officer

JAMES E. ROGAN
Director of the United States Patent and Trademark Office